(12) United States Patent
Beckmann et al.

(10) Patent No.: US 8,545,844 B2
(45) Date of Patent: Oct. 1, 2013

(54) HUMANIZED ANTIBODIES AGAINST HUMAN IL-22RA

(75) Inventors: Roland Beckmann, Vienna (AT); Caroline Johnson-Leger, Saint Sixt (FR)

(73) Assignee: Merck Serona SA, Coinsins, Vaud (CH)

( * ) Notice: Subject to any disclaimer, the term of this patent is extended or adjusted under 35 U.S.C. 154(b) by 0 days.

(21) Appl. No.: 13/510,068

(22) PCT Filed: Nov. 12, 2010

(86) PCT No.: PCT/EP2010/067332
§ 371 (c)(1),
(2), (4) Date: May 16, 2012

(87) PCT Pub. No.: WO2011/061119
PCT Pub. Date: May 26, 2011

(65) Prior Publication Data
US 2012/0230990 A1   Sep. 13, 2012

Related U.S. Application Data

(60) Provisional application No. 61/262,998, filed on Nov. 20, 2009.

(30) Foreign Application Priority Data

Nov. 19, 2009   (EP) ..................... 09176525

(51) Int. Cl.
*A61K 39/395*   (2006.01)
*C12P 21/08*   (2006.01)
*C12N 15/24*   (2006.01)
*C07K 14/54*   (2006.01)

(52) U.S. Cl.
USPC ............. 424/133.1; 435/320.1; 435/328; 435/69.6; 530/387.3; 536/23.53

(58) Field of Classification Search
None
See application file for complete search history.

(56) References Cited

FOREIGN PATENT DOCUMENTS

| WO | WO 2006/047249 | 5/2006 |
|---|---|---|
| WO | WO 2006/100582 | 9/2006 |
| WO | WO 2007/126439 | 11/2007 |

OTHER PUBLICATIONS

Crystal, R. Science, vol. 270, 1995, pp. 404-410.*
Rubanyi (Biol. Aspects Med. (2001) 22:113-142.*
Juengst; British Medical Journal (2003) vol. 326, pp. 1410-1411.*
Dexian Zheng, Cell Research, 2007, vol. 17, pp. 303-306.*
Zhang et al, Cell Research 2007, vol. 17, pp. 89-99.*
Aggarwal, S. et al. "Acinar Cells of the Pancreas Are a Target of Interleukin-22" *Journal of Interferon and Cytokine Research*, 2001, pp. 1047-1053, vol. 21.
Al-Lazikani, B. et al. "Standard Conformations for the Canonical Structures of Immunoglobulins" *Journal of Molecular Biology*, 1997, pp. 927-948, vol. 273.
Andoh, A. et al. "Interleukin-22, a Member of the IL-10 Subfamily, Induces Inflammatory Responses in Colonic Subepithelial Myofibroblasts" *Gastroenterology*, 2005, pp. 969-984, vol. 129.
Aviv, H. et al. "Purification of Biologically Active Globin Messenger RNA by Chromatography on Oligothymidylic acid-Cellulose" *Proceedings of the National Academy of Sciences USA*, Jun. 1972, pp. 1408-1412, vol. 69, No. 6.
Chirgwin, J. et al. "Isolation of Biologically Active Ribonucleic Acid from Sources Enriched in Ribonuclease" *Biochemistry*, 1979, pp. 5294-5299, vol. 18, No. 24.
Chothia, C. et al. "Canonical Structures for the Hypervariable Regions of Immunoglobulins" *Journal of Molecular Biology*, 1987, pp. 901-917, vol. 196.
Dumoutier, L. et al. "Human interleukin-10-related T cell-derived inducible factor: Molecular cloning and functional characterization as an hepatocyte-stimulating factor" *PNAS*, Aug. 29, 2000, pp. 10144-10149, vol. 97, No. 18.
Francis, G. E. et al. "PEGylation of cytokines and other therapeutic proteins and peptides: the importance of biological optimisation of coupling techniques" *International Journal of Hematology*, 1998, pp. 1-18, vol. 68.
Giudicelli, V. et al. "IMGT/GENE-DB: a comprehensive database for human and mouse immunoglobulin and T cell receptor genes" *Nucleic Acids Research*, 2005, pp. D256-D261, vol. 33.
Harris, J. M. et al. "Effect of Pegylation on Pharmaceuticals" *Nature*, Mar. 2003, pp. 214-221, vol. 2.
Ikeuchi, H. et al. "Expression of Interleukin-22 in Rheumatoid Arthritis" *Arthritis & Rheumatism*, Apr. 2005, pp. 1037-1046, vol. 52, No. 4.
Kotenko, S. V. et al. "Identification, Cloning, and Characterization of a Novel Soluble Receptor That Binds IL-22 and Neutralizes Its Activity" *The Journal of Immunology*, 2001, pp. 7096-7103, vol. 166.
Kunz, S. et al. "Interleukin (IL)-19, IL-20 and IL-24 are produced by and act on keratinocytes and are distinct from classical ILs" *Experimental Dermatology*, 2006, pp. 991-1004, vol. 15.
Langer, J. A. et al. "The Class II cytokine receptor (CRF2) family: overview and patterns of receptor-ligand interactions" *Cytokine & Growth Factor Reviews*, 2004, pp. 33-48, vol. 15.
Li, J. et al. "Temporal associations between interleukin 22 and the extracellular domains of IL-22R and IL-10R2" *International Immunopharmacology*, 2004, pp. 693-708, vol. 4.

(Continued)

*Primary Examiner* — Bridget E Bunner
*Assistant Examiner* — Fozia Hamud
(74) *Attorney, Agent, or Firm* — Saliwanchik, Lloyd & Eisenschenk

(57) ABSTRACT

The invention relates to humanized antibodies against human IL-22RA and to their use in the treatment of psoriasis and other immune-mediated diseases such as psoriatic arthritis and atopic dermatitis.

19 Claims, 11 Drawing Sheets

(56) References Cited

OTHER PUBLICATIONS

Moore, K. W. et al. "Interleukin-10 and the Interleukin-10 Receptor" *Annual Review of Immunology*, 2001, pp. 683-765, vol. 19.

Nograles, K. et al. "New insights into the pathogenesis and genetics of psoriatic arthritis" *Nature Clinical Practice Rheumatology*, 2009, pp. 83-91, vol. 5, No. 2.

Nograles, K. E. et al. "IL-22 producing "T22" T-cells account for up-regulated IL-22 in atopic dermatitis (AD), despite reduced IL-17 producing Th17 T-cells" *Journal of Allergy and Clinical Immunology*, Jun. 2009, pp. 1244-1252, vol. 123, No. 6.

Wolk, K. et al. "IL-22 Increases the Innate Immunity of Tissues" *Immunity*, Aug. 2004, pp. 241-254, vol. 21.

Zheng, Y. et al. "Interleukin-22, a $T_H17$ cytokine, mediates IL-23-induced dermal inflammation and acanthosis" *Nature*, Feb. 8, 2007, pp. 648-651, vol. 445.

Jiang, M. et al. "Gene Therapy Using Adenovirus-Mediated Full-length Anti-HER-2 Antibody for HER-2 Overexpression Cancers" *Clinical Cancer Research*, 2006, pp. 6179-6185, vol. 12, No. 20.

\* cited by examiner

Figure 1

```
IGKV4-1      DIVMTQSPDSLAVSLGERATINCKSSQSVLYSSNNKNYLAWYQQKPGQPPKLLIYWASTR
280.46.3.4   DIVMTQSPSSLAVSVGEKVTMSCKSSQSLLYSSNQKNCLAWYQQKPGQSPKLLIYWASSR
             ********.*****.**:.*:.********:*****:** *********.********:*

IGKV4-1      ESGVPDRFSGSGSGTDFTLTISSLQAEDVAVYYCQQYYSTP
280.46.3.4   ESGVPDRFTGSGSGTDFTLTISSVKTEDLAVYYCQQYFSYPFTFGSGTKLEIK
             ********:**************:::**:*******:* *
```

Figure 2

```
IGHV3-66     EVQLVESGGGLVQPGGSLRLSCAASGFTVSSNYMSWVRQAPGKGLEWVSVIY-SGGSTYY
280.46.3.4   EVQLQQSGPELVRPGTSVKISCKASGYSLTADYMNWVKQSPEESLEWIGEINPSTGTTTY
             ****  :**   **:** *::::**  ***:::::::**.**:*:* :.***:.  *  * *:* *

IGHV3-66     ADSVKGRFTISRDNSKNTLYLQMNSLRAEDTAVYYCAR----FDYWGQGTLVTVSS
280.46.3.4   NQKFEAKATLTVDQSSNTAYLQLTSLTSEDSAVYYCARFDAYFDYWGQGTTVTVSS
             :..:.: *:: *:*.** ***:.** :**:******       ******** *****
```

Figure 3

```
IGKV4-1      DIVMTQSPDSLAVSLGERATINCKSSQSVLYSSNNKNYLAWYQQKPGQPPKLLIYWASTR
280.VK4-1-C  DIVMTQSPDSLAVSLGERATINCKSSQSLLYSSNQKNCLAWYQQKPGQPPKLLIYWASSR
             ************************:*****:.** *****************:*

IGKV4-1      ESGVPDRFSGSGSGTDFTLTISSLQAEDVAVYYCQQYYSTP
280.VK4-1-C  ESGVPDRFSGSGSGTDFTLTISSLQAEDVAVYYCQQYFSYPFTFGQGTKVEIK
             *********************************:* *
```

Figure 4

```
280.VH3-66.1 EVQLVESGGGLVQPGGSLRLSCAASGYSLTADYMNWVRQAPGKGLEWIGEINPSTGTTTY
IGHV3-66     EVQLVESGGGLVQPGGSLRLSCAASGFTVSSNYMSWVRQAPGKGLEWVSVIY-SGGSTYY
             *************************:::::::**.***********:. *   * *:* *

280.VH3-66.1 NQKFEARATLTVDQSKNTAYLQMNSLRAEDTAVYYCARFDAYFDYWGQGTLVTVSS
IGHV3-66     ADSVKGRFTISRDNSKNTLYLQMNSLRAEDTAVYYCAR----FDYWGQGTLVTVSS
             :..:. * *:: *:**** ****************       ************
```

Figure 9
```
IGHV3-66      EVQLVESGGGLVQPGGSLRLSCAASGFTVSSNYMSWVRQAPGKGLEWVSVIY-SGGSTYY
280.VH3-66-4  EVQLVESGGGLVQPGGSLRLSCAASGYSLTADYMNWVRQAPGKGLEWIGEINPSTGTTTY
              ************************:::::**.************:.  *   *:*  *
IGHV3-66      ADSVKGRFTISRDNSKNTLYLQMNSLRAEDTAVYYCAR----FDYWGQGTLVTVSS
280.VH3-66-4  NQKFKGRATLSVDQSKNTAYLQMNSLRAEDTAVYYCARFDAYFDYWGQGTLVTVSS
              :..**  *  *:*  *:*********************    ***********
```
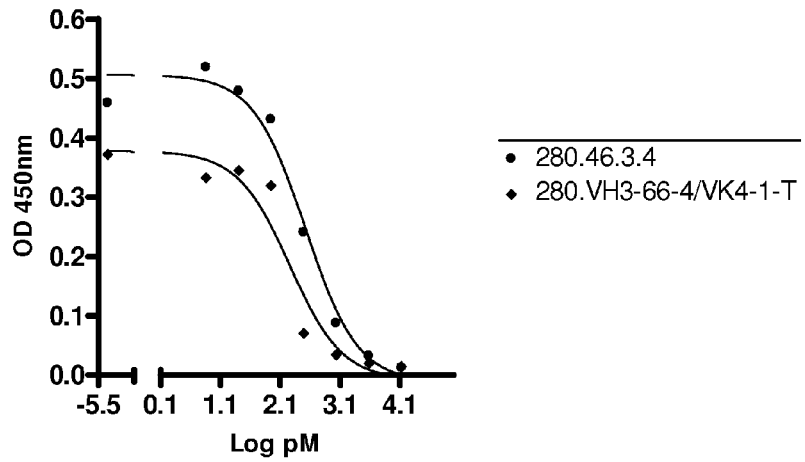
Figure 10
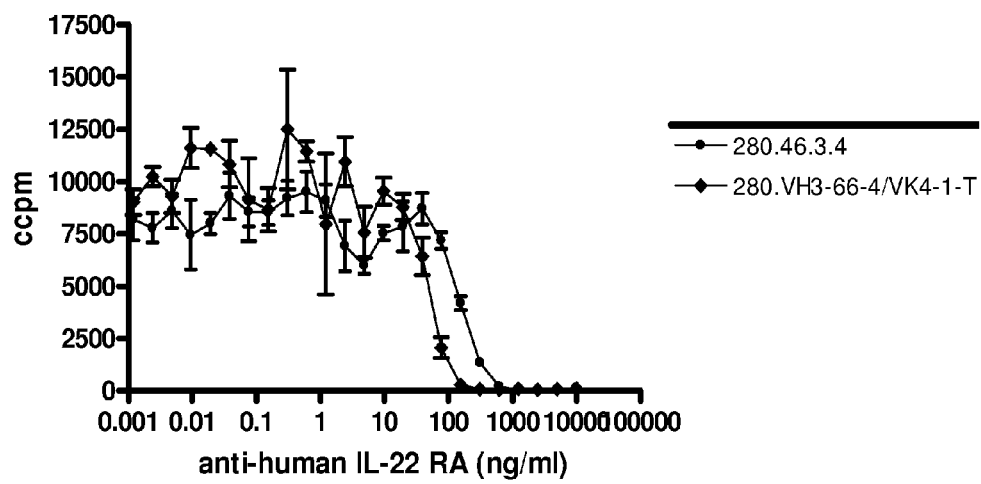
Figure 11

```
28-VH3-66.46    EVQLVESGGGLVQPGGSLRLSCAASGYSITAEYMNWVRQAPGKGLEWIGEINPSTGTTTY
IGHV3-66        EVQLVESGGGLVQPGGSLRLSCAASGFTVSSNYMSWVRQAPGKGLEWVSVIY-SGGSTYY
                ****************************:::::**.************:. *   * *:* *

28-VH3-66.46    NQKFKGRFTISVDQSKNTAYLQMNSLRAEDTAVYYCARFDAYFDYWGQGTLVTVSS
IGHV3-66        ADSVKGRFTISRDNSKNTLYLQMNSLRAEDTAVYYCAR----FDYWGQGTLVTVSS
                :..******* *:**** *******************    *************
```

Figure 17

```
IGKV4-1         DIVMTQSPDSLAVSLGERATINCKSSQSVLYSSNNKNYLAWYQQKPGQPPKLLIYWASTR
280.VK4-1-TSY   DIVMTQSPDSLAVSLGERATINCKSSQSLLYSSNQKNCLAWYQQKPGQPPKLLIYWASSR
                ***********************:****:**:********************:*

IGKV4-1         ESGVPDRFSGSGSGTDFTLTISSLQAEDVAVYYCQQYYSTP
280.VK4-1-TSY   ESGVPDRFSGSGSGTDFTLTISSLQAEDVAVYYCQQYYSYPFTFGQGTKVEIK
                ************************************** *
```

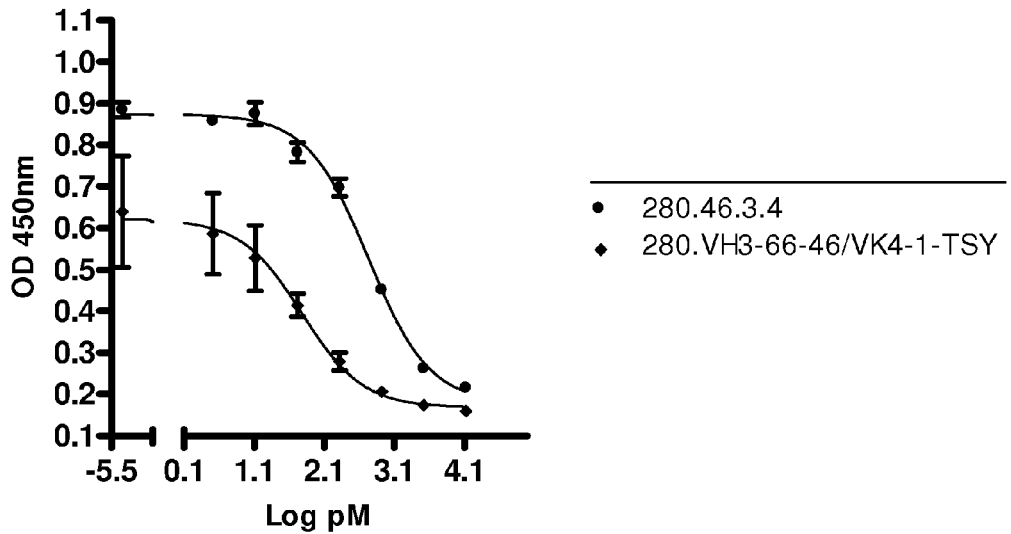

Figure 18

HUMANIZED ANTIBODIES AGAINST HUMAN IL-22RA

CROSS-REFERENCE TO RELATED APPLICATIONS

This application is the U.S. national stage application of International Patent Application No. PCT/EP2010/067332, filed Nov. 12, 2010, which claims the benefit of U.S. Provisional Patent Application No. 61/262,998, filed Nov. 20, 2009.

The Sequence Listing for this application is labeled "RepSeq-List.txt"which was created on Apr. 25, 2013 and is 38 KB. The entire contents of the sequence listing is incorporated herein by reference in its entirety.

FIELD OF THE INVENTION

The present invention relates to humanized antibodies against human IL-22RA and to their use in the treatment of psoriasis and other immune-mediated diseases such as psoriatic arthritis and atopic dermatitis.

BACKGROUND OF THE INVENTION

IL-22RA (also known as IL22R, IL22R1, IL22RA1, CRF2-9 and Zcytor11) belongs to the type II cytokine receptor family and is a component of the receptor for IL-20, IL-22 and IL-24. Due to their structural similarity IL-20, IL-22 and IL-24, together with IL-19 and IL-26, were combined with IL-10 in the so-called "IL-10 family" (Kunz S et al. 2006). IL-10 is a master regulator of the immune response that mediates down-regulation of pro-inflammatory cytokine expression in macrophages, T cells, and other cells of the immune system (Moore K W et al. 2001).

In vitro, IL-20 and IL-24 are produced not only by activated immune cells, but also to a similar extent by keratinocytes. In vivo, these cytokines are expressed preferentially in the inflamed tissues. IL-20 and IL-24 can signal through two receptor complexes, IL-20RA/IL-20RB and IL-22RA/IL-20RB (Langer J A et al. 2004). Several tissues, particularly the skin, tissues from the reproductive and respiratory systems, and various glands appeared to be the main targets of these mediators (Kunz S et al. 2006).

IL-22 was discovered as a gene up-regulated by CD4$^+$ T cells upon activation and it shares 22% amino acid sequence identity with IL-10; it was, thus, originally named IL-10-related T cell-derived inducible factor (IL-TIF) (Dumoutier L et al. 2000). Unlike IL-10, which regulates immune cell functions, IL-22 controls tissue responses to the immune system. IL-22 signals through a heterodimer receptor formed by IL-22RA and IL-10RB which is highly expressed within various tissues but it is not detectable on immune cells. Initially, IL-22 binds via its IL-22RA binding site to the extracellular domain of IL-22RA and, subsequently, IL-10RB binds to a region created by the interaction of IL-22 and IL-22RA to form a cytokine receptor complex with a higher affinity for IL-22 (Li J et al. 2004). Since IL-10RB is broadly expressed by many different cell types, IL-22RA expression is the limiting component that determines IL-22 responsiveness of cells. IL-22RA is expressed strongly in the liver, as well as in the skin, lungs, pancreas and other peripheral tissues (Wolk K et al. 2004; Aggarwal S et al. 2001).

Extensive screening of different cell lines has revealed that only cells which express IL-22RA respond to IL-22, suggesting that there is no alternate receptor that can mediate IL-22 signaling.

A soluble receptor termed IL-22 binding protein (IL-22BP; also known as IL22BP, IL22RA2, IL-22R-alpha2, CRF2X, CRF2—S1 and CRF2-10) is also able to bind to IL-22 as a natural protein antagonist and probably provides systemic regulation of IL-22 activity (Kotenko S V et al. 2003). IL-22 has been found in diseased tissues from patients with different chronic inflammatory diseases that involve infiltrating activated T cells, such as psoriasis, psoriatic arthritis and atopic dermatitis. IL-22 has been most commonly described as a pro-inflammatory cytokine because of its expression in lesions of patients with chronic inflammatory diseases and its induction of pro-inflammatory cytokines such as IL-6, IL-8 and TNF-α (Wolk K et al. 2004; Andoh A et al. 2005; Ikeuchi H et al. 2005; Nograles K E et al. 2009a.; Nograles K E et al. 2009b). Most recently, Zheng et al. showed that IL-22 is important for mediating IL-23-induced dermal inflammation in a mouse model of psoriasis, indicating a pro-inflammatory role (Zheng Y et al. 2007). Given the biological effects of IL-22, including keratinocyte hyperplasia, induction of chemokine and pro-inflammatory cytokine production in certain tissue, the use of antagonists that block, inhibit, reduce or neutralize the activity of IL-22, e.g. by interfering with the receptor binding, may prevent infiltration of pathogenic cells at inflammatory sites. Mouse anti-human IL-22RA monoclonal antibodies have been previously described in PCT patent application WO 2006/047249 filed on Oct. 21, 2005. However, mouse antibodies may cause immunogenicity and humanized anti-human IL-22RA antibodies are desirable. Humanized antibodies generally have at least three potential advantages over mouse antibodies for use in human therapy: (1) because the effector portion is human, it may interact better with the other parts of the human immune system (e.g., destroy the target cells more efficiently by complement-dependent cytotoxicity (CDC) or antibody-dependent cellular cytotoxicity (ADCC)); (2) the human immune system should not recognize the framework or constant region of the humanized antibody as foreign, and therefore the antibody response against such an injected antibody should be less than against a totally foreign mouse antibody; and (3) injected mouse antibodies have been reported to have a half-life in the human circulation much shorter than the half-life of human antibodies. Injected humanized antibodies will presumably have a half-life more similar to naturally occurring human antibodies, allowing smaller and less frequent doses to be given. Thus, in view of the above, there is a need for humanized anti-human IL-22RA antibodies for treating IL-22 mediated inflammation, such as psoriasis, psoriatic arthritis and atopic dermatitis.

SUMMARY OF THE INVENTION

In a first aspect, the invention provides a humanized antibody that binds to human IL-22RA. The humanized antibody of the invention comprises a) a heavy chain variable domain comprising H-CDR1, H-CDR2, and H-CDR3 consisting of amino acid sequences of SEQ ID NO: 1, 2 and 3, respectively and b) a light chain variable domain comprising L-CDR1, L-CDR2, and L-CDR3 consisting of amino acid sequences of SEQ ID NO: 4, 5 and 6, respectively or consisting of amino acid sequences of SEQ ID NO: 4, 5 and 7, respectively. In another aspect, the invention provides an antibody described herein, wherein a) said heavy chain variable domain comprises framework regions H-FR1, H-FR2, H-FR3 and H-FR4 consisting of amino acid sequences of SEQ ID NO: 8, 9, 10 and 11, respectively and b) said light chain variable domain comprises framework regions L-FR1, L-FR2, L-FR3 and L-FR4 consisting of amino acid sequences of SEQ ID NO:

12, 13, 14 and 15, respectively. In another aspect, the invention provides an antibody described herein, wherein a) said heavy chain variable domain consists of amino acid sequence of SEQ ID NO: 16 and b) said light chain variable domain consists of amino acid sequence of SEQ ID NO: 17. In another aspect, the invention provides an antibody described herein, wherein said antibody comprises a) a heavy chain constant region consisting of amino acid sequence of SEQ ID NO: 18 and b) a light chain constant domain consisting of amino acid sequence of SEQ ID NO: 19.

In another aspect, the invention provides a humanized antibody that binds to human IL-22RA which comprises a heavy chain comprising or consisting of amino acid sequence of SEQ ID NO: 20 and a light chain comprising or consisting of amino acid sequence of SEQ ID NO: 21.

In another aspect, the invention provides a polynucleotide, e.g. a DNA, encoding the heavy chain of the humanized antibody according to the present invention. Preferably, said polynucleotide comprises or consists of SEQ ID NO: 22.

In another aspect, the invention provides a polynucleotide, e.g. a DNA, encoding the light chain of the humanized antibody according to the present invention. Preferably, said polynucleotide comprises or consists of SEQ ID NO: 23.

In another aspect, the invention provides a polynucleotide, e.g. a DNA, encoding both the heavy and the light chains of the humanized antibody according to the present invention.

In another aspect, the invention provides a vector and more particularly an expression vector comprising a) a polynucleotide encoding the heavy chain of the humanized antibody according to the present invention and b) a polynucleotide encoding the light chain of the humanized antibody according to the present invention.

In another aspect, the invention provides a vector and more particularly an expression vector comprising a polynucleotide encoding the heavy chain and the light chain of the humanized antibody according to the present invention.

In another aspect, the invention provides a host cell, preferably a CHO cell, comprising, e.g. as a result of a transfection, a vector and in particular an expression vector according to the invention.

In another aspect, the invention provides a method of producing a humanized antibody according to the invention, the method comprising culturing a host cell, preferably a CHO cell, according to the invention and isolating the humanized antibody according to the present invention.

In another aspect, the invention provides a humanized antibody according to the present invention for use as a medicament, in particular for use in the treatment of psoriasis, psoriatic arthritis or atopic dermatitis.

In another aspect, the invention provides a pharmaceutical composition comprising a humanized antibody according to the present invention and its use as a medicament, in particular for use in the treatment of psoriasis, psoriatic arthritis or atopic dermatitis.

In another aspect, the invention provides for the use of a humanized antibody according to the present invention or of a pharmaceutical composition comprising said antibody in the manufacture of a medicament for the treatment of psoriasis, psoriatic arthritis or atopic dermatitis.

DESCRIPTION OF THE FIGURES

FIG. 1 reports the alignment between the human Immunoglobulin germline kappa variable gene 4-1 (IGKV4-1) (SEQ ID NO: 27) and the mouse 280.46.3.4 VL (280.46.3.4) (SEQ ID NO: 35).

FIG. 2 reports the alignment between the human Immunoglobulin germline heavy variable gene 3-66 (IGHV3-66) (SEQ ID NO: 36) and the mouse 280.46.3.4 VH (280.46.3.4) (SEQ ID NO: 25).

FIG. 3 reports the alignment between the human Immunoglobulin germline kappa variable gene 4-1 (IGKV4-1) (SEQ ID NO: 27) and the first version of humanized 280.46.3.4 VL (280.VK4-1-C) (SEQ ID NO: 29).

FIG. 4 reports the alignment between the first version of the humanized 280.46.3.4 VH (280.VH3-66.1) (SEQ ID NO: 30) and the human Immunoglobulin germline heavy variable gene 3-66 (IGHV3-66) (SEQ ID NO: 36).

FIG. 9 reports the alignment between the human Immunoglobulin germline heavy variable gene 3-66 (IGHV3-66) (SEQ ID NO: 36) and version 4 of the humanized 280.46.3.4 VH (280.VH3-66-4) (SEQ ID NO: 33).

FIG. 10 reports the results of the STAT3 phosphorylation assay done in human HepG2 hepatoma cells to compare the potency of the humanized antibody expressed as a human IgG1/kappa, comprising 280.VH3-66-4 paired with 280.VK4-1-T (♦ 280.VH3-66-4/VK4-1-T), with the mouse parental antibody 280.46.3.4 (● 280.46.3.4). The results show that the humanized antibody is 1.8 time more potent than the mouse parental antibody, with $IC_{50}$ values of 183.2 pM and 333.0 pM, respectively.

FIG. 11 reports the results of the proliferation assay done in human IL-22 receptor transfected-BaF3 stable cells to compare the potency of the humanized antibody expressed as a human IgG1/kappa, comprising 280.VH3-66-4 paired with 280.VK4-1-T (♦ 280.VH3-66-4/VK4-1-T), with the mouse parental antibody 280.46.3.4 (● 280.46.3.4). The results show that the humanized antibody is 1.75 time more potent than the mouse parental antibody, with $IC_{50}$ values of 334 pM and 587 pM, respectively.

FIG. 16 reports the alignment between the final humanized VH version, 280.VH3-66-46 (SEQ ID NO: 16), and the human Immunoglobulin germline heavy variable gene 3-66 (IGHV3-66) (SEQ ID NO: 36).

FIG. 17 reports the alignment between the human Immunoglobulin germline kappa variable gene 4-1 (IGKV4-1) (SEQ ID NO: 27) and the final humanized VL version, 280.VK4-1-TSY(SEQ ID NO: 37).

FIG. 18 reports the results of the STAT3 phosphorylation assay done in normal human keratinocytes to compare the potency of the humanized antibody expressed as a human IgG1/kappa, comprising 280.VH3-66-46 paired with 280.VK4-1-TSY (♦ 280.VH3-66-46/VK4-1-TSY), with the mouse parental antibody 280.46.3.4 (● 280.46.3.4). The results show that the humanized antibody (280.346.TSY, see Example 7) is almost 9 times more potent than the mouse parental antibody, with $IC_{50}$ values of 60.95 pM and 541.9 pM, respectively.

DETAILED DESCRIPTION OF THE INVENTION

Figure 5:
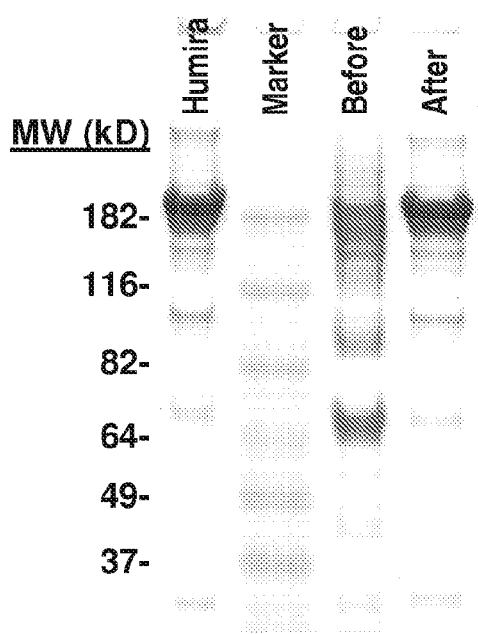
FIG. 5 reports the results of a Coomassie blue staining of protein A-purified humanized 280.46.3.4 antibodies run on an SDS gel under non-denaturing conditions. "Humira"(Adalimumab), a commercialized anti-TNFα monoclonal antibody, is used here as a standard reference. "Marker" is standard protein molecular weight (MW) markers with kD indicated on the left hand side of the figure. "Before" refers to the protein A-purified humanized 280.46.3.4 antibody comprising 280.VH3-66-1 paired with 280.VK4-1-C, containing therefore an unpaired cysteine in the light chain. "After" refers to the protein A-purified humanized 280.46.3.4 antibody comprising 280.VH3-66-1 paired with 280.VK4-1-S.

Prior to setting forth the invention in detail, it may be helpful to the understanding thereof to define the following terms.

As used herein, the term "antibody", and its plural form "antibodies", includes, inter alia, polyclonal antibodies, affinity-purified polyclonal antibodies, monoclonal antibodies, nanobodies and antigen-binding fragments, such as $F(ab')_2$, Fab proteolytic fragments, and single chain variable region fragments (scFvs). Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting non-human CDRs onto human framework and constant regions, or by incorporating the entire non-human variable domains. In some instances, humanized antibodies may retain non-human residues within the human framework regions to enhance proper binding characteristics. Through humanizing antibodies, biological half-life may be increased, and the potential for adverse immune reactions upon administration to humans is reduced.

As used herein, the term "immunoglobulin" (Ig) refers to a protein consisting of one or more polypeptides substantially encoded by immunoglobulin genes. One form of immunoglobulin constitutes the basic structural unit of an antibody. This form is a tetramer and consists of two identical pairs of immunoglobulin chains, each pair having one light and one heavy chain. A light chain has two parts: the variable domain (VL) and the constant domain (CL), which in the context of a light chain can be called constant region as well. A heavy chain has two parts as well: the variable domain (VH) and the constant region (CH). In each pair, the light and heavy chain variable domains are together responsible for binding to an antigen, and the constant regions are responsible for the antibody effector functions.

Full-length immunoglobulin "light chains" (about 25 Kd) are encoded by a variable domain gene at the N-terminus (about 110 amino acids) and a kappa or lambda constant domain (Cκ and Cλ, respectively) gene at the C-terminus. Full-length immunoglobulin "heavy chains" (about 50 Kd), are similarly encoded by a variable domain gene (about 116 amino acids) and one of the other constant region genes (about 330 amino acids) mentioned hereinafter. There are five types of mammalian heavy chain denoted by the Greek letters: α, δ, ε, γ, and μ. The type of heavy chain defines the antibody's isotype as IgA, IgD, IgE, IgG and IgM, respectively. The constant region is identical in all antibodies of the same isotype, but differs in antibodies of different isotypes. Heavy chains γ, α and δ have a constant region composed of three Ig constant domains ($C_H1$, $C_H2$, and $C_H3$), and a hinge region for added flexibility; heavy chains μ and ε have a constant region composed of four Ig constant domains ($C_H1$, $C_H2$, $C_H3$, and $C_H4$) and a hinge region.

An immunoglobulin light or heavy chain variable domain consists of a "framework" region interrupted by three hypervariable regions. Thus, the term "hypervariable region" refers to the amino acid residues of an antibody which are responsible for antigen binding. The hypervariable region comprises amino acid residues from a "Complementarity Determining Region" or "CDR", i.e. L-CDR1, L-CDR2 and L-CDR3 in the light chain variable domain and H-CDR1, H-CDR2 and H-CDR3 in the heavy chain variable domain (Kabat et al. 1991) and/or those residues from a "hypervariable loop" (Chothia and Lesk, 1987). "Framework Region" or "FR" residues are those variable domain residues other than the hypervariable region residues as herein defined. The sequences of the framework regions of different light (i.e. L-FR1, L-FR2, L-FR3 and L-FR4) or heavy (i.e. H-FR1, H-FR2, H-FR3 and H-FR4) chains are relatively conserved within a species. Thus, a "human framework region" is a framework region that is substantially identical (about 85% or more, usually 90-95% or more) to the framework region of a naturally occurring human immunoglobulin. The framework region of an antibody, that is the combined framework regions of the constituent light and heavy chains, serves to position and align the CDRs. The CDRs are primarily responsible for binding to an epitope of an antigen.

Accordingly, the term "humanized" immunoglobulin refers to an immunoglobulin comprising a human framework region and one or more CDRs from a non-human (usually a mouse or rat) immunoglobulin. The non-human immunoglobulin providing the CDRs is called the "donor" and the human immunoglobulin providing the framework is called the "acceptor". Constant regions need not be present, but if they are, they must be substantially identical to human immunoglobulin constant regions, i.e., at least about 85-90%, preferably about 95% or more identical. Hence, all parts of a humanized immunoglobulin, except possibly the CDRs and few residues in the heavy chain constant region if modulation of the effector functions is needed, are substantially identical to corresponding parts of natural human immunoglobulin sequences. A "humanized antibody" is an antibody comprising a humanized light chain variable domain and a humanized heavy chain variable domain. In some instances, humanized antibodies may retain non-human residues within the human framework regions to enhance proper binding characteristics and/or some amino acid mutations may be introduced within the CDRs in order to improve the binding affinity and/or to reduce the immunogenicity and/or to increase the degree of humanness.

The term "recombinant antibodies" means antibodies wherein the amino acid sequence has been varied from that of a native antibody. Because of the relevance of recombinant DNA techniques in the generation of antibodies, one need not be confined to the sequences of amino acids found in natural antibodies; antibodies can be redesigned to obtain desired characteristics. The possible variations are many and range from the changing of just one or a few amino acids to the complete redesign of, for example, the variable domain or constant region. Changes in the constant region will, in general, be made in order to improve, reduce or alter characteristics, such as complement fixation (e.g. complement dependent cytotoxicity, CDC), interaction with membranes and other effector functions (e.g. antibody dependent cellular cytotoxicity, ADCC). Changes in the variable domain will be made in order to improve the antigen binding characteristics.

In addition to antibodies, immunoglobulins may exist in a variety of other forms including, for example, single-chain or Fv, Fab, and (Fab')$_2$, as well as diabodies, linear antibodies, multivalent or multispecific hybrid antibodies. As used herein, the terms "single-chain Fv," "single-chain antibodies," "Fv" or "scFv" refer to antibody fragments that comprises the variable domains from both the heavy and light chains, but lacks the constant regions, but within a single polypeptide chain. Generally, a single-chain antibody further comprises a polypeptide linker between the VH and VL domains which enables it to form the desired structure which would allow for antigen binding. In specific embodiments, single-chain antibodies can also be bi-specific and/or humanized. A "Fab fragment" is comprised of one light chain and the variable and C$_H$1 domains of one heavy chain. The heavy chain of a Fab molecule cannot form a disulfide bond with another heavy chain molecule. A "Fab' fragment" contains one light chain and one heavy chain that contains more of the constant region, between the C$_H$1 and C$_H$2 domains, such that an interchain disulfide bond can be formed between two heavy chains to form a F(ab')$_2$ molecule. A "F(ab')$_2$" contains two light chains and two heavy chains containing a portion of the constant region between the C$_H$1 and C$_H$2 domains, such that an interchain disulfide bond is formed between two heavy chains. Having defined some important terms, it is now possible to focus the attention on particular embodiments of the instant invention.

The present invention is based upon the discovery of humanized anti-human IL-22RA antibodies. Use of these antibodies as antagonists to IL-22RA can inhibit inflammation and, therefore, can be useful in the treatment of chronic inflammatory diseases that involve infiltrating activated T cells, such as psoriasis, psoriatic arthritis and atopic dermatitis. The invention provides the use of humanized antibodies that recognize, bind, modulate and/or neutralize the IL-22RA. In particular, the invention provides the use of humanized light and heavy chain variable domains that recognize, bind, modulate and/or neutralize the IL-22RA. Such humanized light and heavy chain variable domains can be fused, respectively, to a kappa or lambda constant domain and to a constant region of heavy chain chosen among any isotype (IgA, IgD, IgE, IgG and IgM), and expressed in a variety of host cells. Preferably, the constant region chosen is that of an IgG, and more preferably of an IgG1. The humanized anti-IL-22RA antibodies described herein were generated using, as starting point of the humanization process, amino acid sequences of mouse anti-human IL-22RA monoclonal antibodies previously described in PCT patent application WO 2006/047249 filed on Oct. 21, 2005.

IL-22RA is a type II cytokine receptor described, for the first time, as Zcytor11, in PCT patent application WO 99/07848 filed on Jul. 30, 1998. The amino acid sequence of human IL-22RA is shown in SEQ ID NO: 24.

The present invention also provides humanized IL-22RA antibodies that bind to polypeptide fragments or peptides comprising an epitope-bearing portion of a IL-22RA polypeptide or an immunogenic epitope or antigenic epitope. The binding of the antibodies to these epitopes results in inhibition, blocking, neutralization, and/or reduction in signal transduction of IL-22RA.

The activity of the antibodies as described herein can be measured by their ability to inhibit, or reduce proliferation using a variety of assays that measure proliferation of and/or binding to cells expressing the IL-22RA receptor. Of particular interest are changes in IL-22-dependent cells. Suitable cell lines to be engineered to be IL-22-dependent include the BaF3 cell line. The activity of the humanized anti-IL-22RA antibodies can also be measured in the BaF3 proliferation assay, STAT3 phosphorylation assay in human HepG2 hepatoma cells or in mouse HEPA1-6 hepatoma cells, the Biacore assay, or the normal human keratinocyte assay described hereinafter.

In an embodiment, the humanized antibody of the invention comprises a) a heavy chain variable domain comprising H-CDR1, H-CDR2, and H-CDR3 consisting of amino acid sequences of SEQ ID NO: 1, 2 and 3, respectively and b) a light chain variable domain comprising L-CDR1, L-CDR2, and L-CDR3 consisting of amino acid sequences of SEQ ID NO: 4, 5 and 6, respectively or consisting of amino acid sequences of SEQ ID NO: 4, 5 and 7, respectively.

In another embodiment, the invention provides an antibody described herein, wherein a) said heavy chain variable domain comprises framework regions H-FR1, H-FR2, H-FR3 and H-FR4 consisting of amino acid sequences of SEQ ID NO: 8, 9, 10 and 11, respectively and b) said light chain variable domain comprises framework regions L-FR1, L-FR2, L-FR3 and L-FR4 consisting of amino acid sequences of SEQ ID NO: 12, 13, 14 and 15, respectively.

In another embodiment, the invention provides an antibody described herein, wherein a) said heavy chain variable domain consists of amino acid sequence of SEQ ID NO: 16 and b) said light chain variable domain consists of amino acid sequence of SEQ ID NO: 17.

In another embodiment, the invention provides an antibody described herein, wherein a) said heavy chain variable domain is fused to a heavy chain constant region selected from the group consisting of the constant region of a human IgA, IgG, IgM, IgD, IgE or any subclass, preferably an IgG1 and b) said light chain variable domain is fused to a constant domain of a k or λ human immunoglobulin light chain, preferably a k.

In another embodiment, said heavy chain constant region comprises some amino acid mutations that modulate, reduce or inhibit the antibody effector function (e.g. antibody dependent cellular toxicity (ADCC) and complement dependent cytotoxicity (CDC)).

In another embodiment, the invention provides an antibody described herein, wherein said antibody comprises a) a heavy chain constant region consisting of amino acid sequence of SEQ ID NO: 18 and b) a light chain constant domain consisting of amino acid sequence of SEQ ID NO: 19.

In another embodiment, the invention provides a humanized antibody that binds to human IL-22RA which comprises a heavy chain comprising or consisting of amino acid sequence of SEQ ID NO: 20 and a light chain comprising or consisting of amino acid sequence of SEQ ID NO: 21.

Methods for preparing the polynucleotides encoding the antibodies described herein (including DNA and RNA) are well known in the art. Total RNA can be prepared using guanidinium isothiocyanate extraction followed by isolation by centrifugation in a CsCl gradient (Chirgwin J M et al. 1979). Poly(A)+ RNA is prepared from total RNA using the method of Aviv and Leder (Aviv H et al. 1972). Complementary DNA (cDNA) is prepared from poly(A)+ RNA using known methods. In the alternative, genomic DNA can be isolated. Polynucleotides encoding IL-22RA antibodies are then identified and isolated by, for example, hybridization or PCR.

The antibodies disclosed herein may be produced by any technique known in the art, such as by recombinant technologies, chemical synthesis, cloning, ligations, or combinations thereof. In a embodiment, the antibodies of the present invention are produced by recombinant technologies, e.g., by expression of a corresponding nucleic acid in a suitable host cell. The polypeptide produced may be glycosylated or not, or may contain other post-translational modifications depending on the host cell type used. Many books and reviews provide teachings on how to clone and produce recombinant proteins using vectors and prokaryotic or eukaryotic host cells.

A further embodiment of the present invention is therefore an isolated nucleic acid molecule encoding any of the antibodies or portion thereof here above or below described, or a complementary strand or degenerate sequence thereof. In this regard, the term "nucleic acid molecule" encompasses all different types of nucleic acids, including without limitation deoxyribonucleic acids (e.g., DNA, cDNA, gDNA, synthetic DNA, etc.), ribonucleic acids (e.g., RNA) and peptide nucleic acids (PNA). In a preferred embodiment, the nucleic acid molecule is a DNA molecule, such as a double-stranded DNA molecule or a cDNA molecule. The term "isolated" means nucleic acid molecules that have been identified and separated from at least one contaminant nucleic acid molecule with which it is ordinarily associated in the natural source. An isolated nucleic acid molecule is other than in the form or setting in which it is found in nature. Isolated nucleic acid molecules therefore are distinguished from the specific nucleic acid molecule as it exists in natural cells. A degenerate sequence designates any nucleotide sequence encoding the same amino acid sequence as a reference nucleotide sequence, but comprising a distinct nucleotide sequence as a result of the genetic code degeneracy.

In another embodiment a nucleic acid molecule, also called polynucleotide, encodes the heavy chain of the humanized antibody of the invention and another polynucleotide encodes the light chain of the humanized antibody of the invention.

In a preferred embodiment the polynucleotide encoding the heavy chain of the humanized antibody of the invention comprises or consists of SEQ ID NO: 22.

In a preferred embodiment the polynucleotide encoding the light chain of the humanized antibody of the invention comprises or consists of SEQ ID NO: 23.

In a preferred embodiment a unique polynucleotide encodes for both the heavy and light chain of the humanized antibody of the invention.

A further embodiment of this invention is a vector comprising DNA encoding any of the above or below described antibodies or portion thereof. The vector may be any cloning or expression vector, integrative or autonomously replicating, functional in any prokaryotic or eukaryotic cell. In particular, the vector may be a plasmid, cosmid, virus, phage, episome, artificial chromosome, and the like. The vector may comprise the coding sequences for both the heavy and light chain, or either of the light and heavy chain coding sequences. Should the vector comprise coding sequences for both heavy and light chains, the heavy and light chains may each be operably linked to a promoter. The promoter may be the same or different for the heavy and light chain. The heavy and light chain may also be operably linked to one single promoter, in this case the coding sequences for the heavy and light chains may preferably be separated by an internal ribosomal entry site (IRES). Suitable promoters for eukaryotic gene expression are, for example, promoters derived from viral genes such as the murine or human cytomegalovirus (CMV), the mouse bi-directional CMV promoter or the rous sarcoma virus (RSV) promoter, which are well known to the person skilled in the art. The vector may comprise regulatory elements, such as a promoter, terminator, enhancer, selection marker, origin of replication, insulator etc. The appropriate nucleic acid sequence may be inserted into the vector by a variety of procedures. In general, DNA is inserted into an appropriate restriction endonuclease site(s) using techniques known in the art. Construction of suitable vectors containing one or more of these components employs standard ligation techniques which are known to the skilled artisan.

A further embodiment of the present invention is a recombinant host cell, wherein said cell comprises a nucleic acid molecule/polynucleotide or a vector as defined above. The host cell may be a prokaryotic or eukaryotic cell. Examples of prokaryotic cells include bacteria, such as *E. coli*. Examples of eukaryotic cells are yeast cells, plant cells, mammalian cells and insect cells including any primary cell culture or established cell line (e.g., 3T3, Vera, HEK293, TN5, etc.). Suitable host cells for the expression of glycosylated proteins are derived from multicellular organisms. Examples of useful mammalian host cell lines include Chinese hamster ovary (CHO) and COS cells. Particularly preferred mammalian cells of the present invention are CHO cells.

As disclosed here above, the antibodies of the present invention may be produced by any technique known in the art, such as by recombinant technologies, chemical synthesis, cloning, ligations, or combinations thereof.

Another embodiment of this invention is therefore a method of producing an antibody of the present invention, the method comprising culturing a recombinant host cell of the invention under conditions allowing expression of the nucleic acid molecule, and recovering/isolating the polypeptide produced. The polypeptide produced may be glycosylated or not, or may contain other post-translational modifications depending on the host cell type used. The method of producing an antibody of the present invention may further comprise the step of formulating the antibody into a pharmaceutical composition.

A further embodiment of the present invention is therefore a pharmaceutical composition comprising the humanized antibody according to the invention. Preferably, said pharmaceutical composition may further comprise additional excipients, such as buffer, stabilizer, surfactant, etc.

Pharmaceutical compositions according to the invention are useful in the diagnosis, prevention, and/or treatment (local or systemic) of psoriasis and other immune-mediated diseases such as psoriatic arthritis and atopic dermatitis.

The term "treatment" within the context of this invention refers to any beneficial effect on progression of disease, including attenuation, reduction, decrease or diminishing of the pathological development after onset of disease.

The pharmaceutical compositions of the invention may be administered with a pharmaceutically acceptable carrier.

The term "pharmaceutically acceptable" is meant to encompass any carrier, which does not interfere with effectiveness of the biological activity of the active ingredient and that is not toxic to the host to which it is administered. For example, for parenteral administration, the active protein(s) may be formulated in a unit dosage form for injection in vehicles such as saline, dextrose solution, serum albumin and Ringer's solution.

In another aspect, the invention provides a pharmaceutical composition according to the invention for use as a medicament. In another aspect, the invention provides a method of treating a disease in a patient, comprising administering to the patient a pharmaceutical composition according to the invention. Preferably, the disease is selected from psoriasis, psoriatic arthritis and atopic dermatitis.

In another aspect, the invention provides a humanized antibody according to the invention for use as a medicament. In another aspect, the invention provides a method of treating a disease in a patient, comprising administering to the patient a humanized antibody according to the invention. Preferably, the disease is selected from psoriasis, psoriatic arthritis and atopic dermatitis.

In another aspect, the invention provides for the use of humanized antibody according to the invention for the preparation of a medicament for the treatment of psoriasis, psoriatic arthritis or atopic dermatitis.

In a first use according to the invention, a pharmaceutical composition according to the invention is administered pulmonary.

In a second use according to the invention, a pharmaceutical composition according to the invention is administered intranasally.

In a third use according to the invention, a pharmaceutical composition according to the invention is administered by inhalation.

In a fourth use according to the invention, a pharmaceutical composition according to the invention is administered orally.

In a fifth use according to the invention, a pharmaceutical composition according to the invention is administered intravenously or intramuscularly.

In a preferred embodiment, in a use according to the invention, a pharmaceutical composition according to the invention is administered subcutaneously.

A pharmaceutical composition according to the invention is administered according to any one of the routes described above daily or every other day.

For parenteral (e.g. intravenous, subcutaneous, intramuscular) administration, a pharmaceutical composition of the invention can be formulated as a solution, suspension, emulsion or lyophilized powder in association with a pharmaceutically acceptable parenteral vehicle (e.g. water, saline, dextrose solution) and additives that maintain isotonicity (e.g. mannitol) or chemical stability (e.g. preservatives and buffers). The formulation is sterilized by commonly used techniques.

The active ingredients of the pharmaceutical composition according to the invention can be administered to an individual in a variety of ways. The routes of administration may include intradermal, transdermal (e.g. in slow release formulations), intramuscular, intraperitoneal, intravenous, subcutaneous, epidural, topical, oral routes and by aerosol administration, intranasal route or inhaled. Any other therapeutically efficacious route of administration can be used, for example absorption through epithelial or endothelial tissues or by gene therapy wherein a DNA molecule encoding the active agent is administered to the patient (e.g. via a vector), which causes the active agent to be expressed and secreted in vivo. In addition, a pharmaceutical composition according to the invention can be administered together with other components of biologically active agents such as pharmaceutically acceptable surfactants, excipients, carriers, diluents and vehicles.

The dosage administered to an individual will vary depending upon a variety of factors, including pharmacokinetic properties, the route of administration, patient conditions and characteristics (sex, age, body weight, health, size), extent of symptoms, concurrent treatments, frequency of treatment and the effect desired.

The antibodies of the present invention can be produced, formulated, administered or used in other alternative forms that can be preferred according to the desired method of use and/or production. Useful conjugates or complexes can also be generated for improving the agents in terms of drug delivery efficacy. For this purpose, the antibodies described herein can be in the form of active conjugates or complex with molecules such as polyethylene glycol and other natural or synthetic polymers (Harris J M et al. 2003). In this regard, the present invention contemplates chemically modified antibodies, in which the antibody is linked with a polymer. Typically, the polymer is water soluble so that the conjugate does not precipitate in an aqueous environment, such as a physiological environment. Moreover, a mixture of polymers can be used to produce the conjugates. The conjugates used for therapy can comprise pharmaceutically acceptable water-soluble polymer moieties. Suitable water-soluble polymers include polyethylene glycol (PEG), monomethoxy-PEG, aryloxy-PEG, bis-succinimidyl carbonate PEG, propylene glycol homopolymers, a polypropylene oxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A conjugate can also comprise a mixture of such water-soluble polymers. Examples of conjugates comprise any of the antibody disclosed here above and a polyalkyl oxide moiety attached to the N-terminus. PEG is one suitable polyalkyl oxide. As an illustration, any of the antibody disclosed herein can be modified with PEG, a process known as "PEGylation". PEGylation can be carried out by any of the PEGylation reactions known in the art (Francis G E et al. 1998). For example, PEGylation can be performed by an acylation reaction or by an alkylation reaction with a reactive polyethylene glycol molecule. Preferably, all these modifications do not affect significantly the ability of the antibody to bind human IL-22RA.

The present invention also includes recombinant humanized antibodies against human IL-22RA that are functionally equivalent to those described above. Modified humanized antibodies providing improved stability and/or therapeutic efficacy are also included. Examples of modified antibodies include those with conservative substitutions of amino acid residues, and one or more deletions or additions of amino acids which do not significantly deleteriously alter the antigen binding utility. Substitutions can range from changing or modifying one or more amino acid residues to complete redesign of a region as long as the therapeutic utility is maintained. Humanized antibodies of the present invention can be modified post-translationally (e.g., acetylation, and phosphorylation) or can be modified synthetically (e.g., the attachment of a labeling group). It is understood that the humanized antibodies designed by the present method may have additional conservative amino acid substitutions which have substantially no effect on antigen binding or other immunoglobulin functions.

The humanized antibodies of the present invention can include derivatives that are modified, for example, but not by way of limitation, the derivatives include humanized antibodies, that have been modified, e.g., by glycosylation, acetylation, pegylation, phosphylation, amidation, derivatization by known protecting/blocking groups, proteolytic cleavage, linkage to a cellular ligand or other protein, etc. Additionally, the derivative may contain one or more non-classical and/or non-natural amino acids. The in vivo half-lives of the humanized antibodies of the present invention can be increased by modifying (e.g., substituting, deleting or adding) amino acid residues identified as involved in the interaction between the Fc region and the FcRn receptor.

All references cited herein, including journal articles or abstracts, published or unpublished U.S. or foreign patent application, issued U.S. or foreign patents or any other references, are entirely incorporated by reference herein, including all data, tables, figures and text presented in the cited references. Additionally, the entire contents of the references cited within the references cited herein are also entirely incorporated by reference.

The foregoing description of the specific embodiments will so fully reveal the general nature of the invention that others can, by applying knowledge within the skill of the art (including the contents of the references cited herein), readily modify and/or adapt for various application such specific embodiments, without undue experimentation, without departing from the general concept of the present invention. Therefore, such adaptations and modifications are intended to be within the meaning of a range of equivalents of the disclosed embodiments, based on the teaching and guidance presented herein. It is to be understood that the phraseology or terminology herein is for the purpose of description and not of limitation.

EXAMPLES

Example 1

Selection of the Starting Antibody for the Humanization Process

The mouse anti-human IL-22RA monoclonal antibodies expressed by the five hybridomas described in Example 18 of the PCT patent application WO 2006/047249 filed on Oct. 21, 2005 were compared in order to select the one to be used as starting point of the humanization process. The most important criteria for the selection were: high affinity for human IL-22RA, cross-reactivity with murine IL-22RA, no cross-reactivity with IL-22BP and no agonistic activity for human IL-22RA. Only one antibody met all the criteria above (data not shown), i.e. the antibody expressed by the hydridoma called 280.46.3.4 (ATCC Patent Deposit Designation PTA-6284) which is a mouse IgG1/kappa antibody.

The specific amino acid sequence of the variable domain of the heavy and light chains (VH and VL, respectively) of this mouse anti-human IL-22RA monoclonal antibody (hereinafter called "mouse 280.46.3.4") are recited in SEQ ID NO: 25 and 26, respectively.

Example 2

Design of Reshaped Humanized 280.46.3.4 Variable Domains

A. Selection of Homologous Human Germline for Framework Sequence

Using the IMGT-GENE database (Giudicelli V. et al. 2005) human germline kappa light chain variable domains whose overall sequences (frameworks and CDRs) showed a high percent identity to those of mouse 280.46.3.4 VL were identified by comparison of amino acid sequences. Mouse 280.46.3.4 VL was most homologous to human Immunoglobulin germline kappa variable gene 4-1 (IGKV4-1) showing an identity of 82.2% (83 amino acid residues out of 101; FIG. 1). IGKV4-1, recited in SEQ ID NO: 27, was therefore chosen as human framework acceptor sequence for CDR-grafting. For the mouse 280.46.3.4 VH, no high percent identity human germline was identified using IMGT-GENE database. Human Immunoglobulin germline heavy variable gene 1-46 (IGHV1-46) human germline was identified as having the highest homology with 60.2% identity (59 amino acid residues out of 98). However, IGHV3-66, recited in SEQ ID NO: 28, was effectively selected as human framework acceptor sequence despite its lowest homology (50.0% identity, 49 amino acid residues out of 98; FIG. 2) since its sequence is close to that of mouse 280.46.3.4 VH in various important framework positions and is therefore likely to offer good stability.

B. Amino Acid Substitutions in Framework Regions

B.1 Light Chain

The next step in the design for the humanized 280.46.3.4 VL was to join the CDRs from the mouse 280.46.3.4 VL to the frameworks regions (FRs) from human germline IGKV4-1. The immunoglobulin kappa joining 1 human germline gene (IGKJ1) was used instead of the mouse J gene. In the first version of reshaped humanized 280.46.3.4 VL (280.VK4-1-C), recited in SEQ ID NO: 29, no changes were made in the human FRs, i.e. none of the mouse residues in the FRs were thought to be structurally important. The alignment between the IGKV4-1 and the first version of humanized 280.46.3.4 VL (280.VK4-1-C) is shown in FIG. 3.

B.2 Heavy Chain

The next step in the design process for the humanized 280.46.3.4 VH was to join the CDRs from mouse 280.46.3.4 VH to the FRs from human germline IGHV3-66. In the first version of reshaped humanized 280.46.3.4 VH (280.VH3-66.1), recited in SEQ ID NO: 30, 12 changes were made in the human framework regions (FIG. 4). The 12 changes in the human FRs were at positions 27, 28, 29, 30, 48, 49, 67, 69, 70, 71, 73 and 78 (see numbering in Table 1).

TABLE 1

Alignment of amino acid sequences leading to the design of humanized 280.46.3.4 VH

| Kabat numbering | Chothia numbering | Mouse 280.46.3.4 VH | IGHV3-66 | Humanized 280.VH3-66-46 |
|---|---|---|---|---|
| (H-FR1) 1 | 1 | E | E | E |
| 2 | 2 | V | V | V |
| 3 | 3 | Q | Q | Q |
| 4 | 4 | L | L | L |
| 5 | 5 | Q | V | V |
| 6 | 6 | Q | E | E |
| 7 | 7 | S | S | S |
| 8 | 8 | G | G | G |
| 9 | 9 | P | G | G |
| 10 | 10 | E | G | G |
| 11 | 11 | L | L | L |
| 12 | 12 | V | V | V |
| 13 | 13 | R | Q | Q |
| 14 | 14 | P | P | P |
| 15 | 15 | G | G | G |
| 16 | 16 | T | G | G |
| 17 | 17 | S | S | S |
| 18 | 18 | V | L | L |
| 19 | 19 | K | R | R |
| 20 | 20 | I | L | L |
| 21 | 21 | S | S | S |
| 22 | 22 | C | C | C |
| 23 | 23 | K | A | A |
| 24 | 24 | A | A | A |
| 25 | 25 | S | S | S |
| 26 | (H-CDR1) 26 | G | G | G |
| 27 | 27 | Y | F | Y |
| 28 | 28 | S | T | S |
| 29 | 29 | L | V | I |
| (H-FR1) 30 | 30 | T | S | T |
| (H-CDR1) 31 | 31 | A | S | A |
| 32 | (H-CDR1) 32 | D | N | E |
| 33 | 33 | Y | Y | Y |
| 34 | 34 | M | M | M |
| (H-CDR1) 35 | 35 | N | S | N |
| (H-FR2) 36 | 36 | W | W | W |
| 37 | 37 | V | V | V |
| 38 | 38 | K | R | R |
| 39 | 39 | Q | Q | Q |
| 40 | 40 | S | A | A |

TABLE 1-continued

Alignment of amino acid sequences leading to the design of humanized 280.46.3.4 VH

| Kabat numbering | Chothia numbering | Mouse 280.46.3.4 VH | IGHV3-66 | Humanized 280.VH3-66-46 |
|---|---|---|---|---|
| 41 | 41 | P | P | P |
| 42 | 42 | E | G | G |
| 43 | 43 | E | K | K |
| 44 | 44 | S | G | G |
| 45 | 45 | L | L | L |
| 46 | 46 | E | E | E |
| 47 | 47 | W | W | W |
| 48 | 48 | I | V | I |
| (H-FR2) 49 | 49 | G | S | G |
| (H-CDR2) 50 | 50 | E | V | E |
| 51 | 51 | I | I | I |
| 52 | (H-CDR2) 52 | N | Y | N |
| 52A | 52A | P | — | P |
| 53 | 53 | S | S | S |
| 54 | 54 | T | G | T |
| 55 | 55 | G | G | G |
| 56 | (H-CDR2) 56 | T | S | T |
| 57 | 57 | T | T | T |
| 58 | 58 | T | Y | T |
| 59 | 59 | Y | Y | Y |
| 60 | 60 | N | A | N |
| 61 | 61 | Q | D | Q |
| 62 | 62 | K | S | K |
| 63 | 63 | F | V | F |
| 64 | 64 | E | K | K |
| (H-CDR2) 65 | 65 | A | G | G |
| (H-FR3) 66 | 66 | K | R | R |
| 67 | 67 | A | F | F |
| 68 | 68 | T | T | T |
| 69 | 69 | L | I | I |
| 70 | 70 | T | S | S |
| 71 | 71 | V | R | V |
| 72 | 72 | D | D | D |
| 73 | 73 | Q | N | Q |
| 74 | 74 | S | S | S |
| 75 | 75 | S | K | K |
| 76 | 76 | N | N | N |
| 77 | 77 | T | T | T |
| 78 | 78 | A | L | A |
| 79 | 79 | Y | Y | Y |
| 80 | 80 | L | L | L |
| 81 | 81 | Q | Q | Q |
| 82 | 82 | L | M | M |
| 82A | 82A | T | N | N |
| 82B | 82B | S | S | S |
| 82C | 82C | L | L | L |
| 83 | 83 | T | R | R |
| 84 | 84 | S | A | A |
| 85 | 85 | E | E | E |
| 86 | 86 | D | D | D |
| 87 | 87 | S | T | T |
| 88 | 88 | A | A | A |
| 89 | 89 | V | V | V |
| 90 | 90 | Y | Y | Y |
| 91 | 91 | Y | Y | Y |
| 92 | 92 | C | C | C |
| 93 | 93 | A | A | A |
| (H-FR3) 94 | 94 | R | R | R |
| (H-CDR3) 95 | (H-CDR3) 95 | F | | F |
| 96 | 96 | D | | D |
| 97 | 97 | A | | A |
| 98 | 98 | Y | | Y |
| 99 | 99 | | | F |
| 100 | 100 | F | F | — |
| 101 | 101 | D | D | D |
| (H-CDR3) 102 | (H-CDR3) 102 | Y | Y | Y |
| (H-FR4)103 | 103 | W | W | W |
| 104 | 104 | G | G | G |
| 105 | 105 | Q | Q | Q |
| 106 | 106 | G | G | G |
| 107 | 107 | T | T | T |
| 108 | 108 | T | L | L |
| 109 | 109 | V | V | V |
| 110 | 110 | T | T | T |
| 111 | 111 | V | V | V |
| 112 | 112 | S | S | S |
| (H-FR4)113 | 113 | S | S | S |

The first column (Kabat numbering) gives the residue number according to Kabat (Kabat et al. 1991). FR and CDR identify the framework regions (H-FR1, H-FR2, H-FR3, and H-FR4) and the complementarity-determining regions (H-CDR1, H-CDR2, and H-CDR3) of the heavy chain variable domain, with the three CDRs separating the four FRs. The second column (Chothia numbering) gives the residue number according to Chothia's CDRs definition (Al-Lazikani et al. 1997). The third column (mouse 280.46.3.4 VH) gives the amino acid sequence of the heavy chain variable domain of mouse 280.46.3.4. The fourth column (IGHV3-66) gives the amino acid sequence of human Immunoglobulin germline Heavy Variable gene 3-66 (accession number IMGT X92218) used as human acceptor framework for CDR-grafting. The fifth column (Humanized 280.VH3-66-46) gives the amino acid sequence of the final humanized version of mouse 280.46.3.4 VH; the residues underlined indicate the amino acids that differ from human germline IGHV3-66.

At position 27, 28, 29 and 30 in H-FR1, the amino acids present in human germline IGHV3-66 were changed to the amino acids found at those positions in the mouse 280.46.3.4 VH. Although these positions are designated as being within H-FR1 (Kabat numbering; Table 1), positions 26 to 30 are part of the structural loop that forms the H-CDR1 loop of the VH. It is likely therefore that the amino acids at these positions are directly involved in binding to antigen. Indeed, positions 27 to 30 are part of the canonical structure for H-CDR1 as defined by Chothia (Table 1).

At positions 48 and 49 in H-FR2, the amino acids present in human germline IGHV3-66 (valine and serine, respectively) were changed to the amino acids found at those positions in mouse 280.46.3.4 VH (isoleucine and glycine, respectively; Table 1). These two residues are very close to the H-CDR2 and influence the fine structure of the CDR loop.

At positions 67, 69, 70, 73 and 78 in H-FR3, the amino acids present in human germline IGHV3.66 (phenylalanine, isoleucine, serine, asparagine and leucine, respectively) were changed to the amino acids found at those positions in mouse 280.46.3.4 VH (alanine, leucine, threonine, glutamine and alanine, respectively; Table 1). These 5 residues are important in the packing of the VL and VH domains and most likely influence the overall stability of the antibody.

At position 71 in H-FR3, the arginine present in human germline IGHV3-66 was changed to a valine as found at that position in mouse 280.46.3.4 VH. Position 71 is part of the canonical structure for H-CDR2 as defined by Chothia (Table 1). Substitution of an arginine for a valine at this position would very probably disrupt the placing of the H-CDR2 loop.

Example 3

Removal of Free Cysteine in the CDR1 of the Light Chain

There is an unpaired cysteine in the CDR1 of the light chain (L-CDR1) at Kabat position 32 (see numbering in Table 2) which has been associated with high level of covalent aggregate formation during expression and purification of the humanized 280.46.3.4 antibody comprising 280.VH3-66-1 paired with 280.VK4-1-C (data not shown).

TABLE 2

Alignment of amino acid sequences leading to the design of humanized 280.46.3.4 VL

| Kabat & Chothia Numbering | Mouse 280.46.3.4 VL | IGKV4-1 | Humanized 280.VK4-1-TSY |
|---|---|---|---|
| (L-FR1) 1 | D | D | D |
| 2 | I | I | I |
| 3 | V | V | V |
| 4 | M | M | M |
| 5 | T | T | T |
| 6 | Q | Q | Q |
| 7 | S | S | S |
| 8 | P | P | P |
| 9 | S | D | D |
| 10 | S | S | S |
| 11 | L | L | L |
| 12 | A | A | A |
| 13 | V | V | V |
| 14 | S | S | S |
| 15 | V | L | L |
| 16 | G | G | G |
| 17 | E | E | E |
| 18 | K | R | R |
| 19 | V | A | A |
| 20 | T | T | T |
| 21 | M | I | I |
| 22 | S | N | N |
| (L-FR1) 23 | C | C | C |
| (L-CDR1) 24 | K | K | K |
| 25 | S | S | S |
| 26 | S | S | S |
| 27 | Q | Q | Q |
| 27A | S | S | S |
| 27B | L | V | L |
| 27C | L | L | L |
| 27D | Y | Y | Y |
| 27E | S | S | S |
| 27F | S | S | S |
| 28 | N | N | N |
| 29 | Q | N | Q |
| 30 | K | K | K |
| 31 | N | N | N |
| 32 | C | Y | T |
| 33 | L | L | L |
| (L-CDR1) 34 | A | A | A |
| (L-FR2) 35 | W | W | W |
| 36 | Y | Y | Y |
| 37 | Q | Q | Q |
| 38 | Q | Q | Q |
| 39 | K | K | K |
| 40 | P | P | P |
| 41 | G | G | G |
| 42 | Q | Q | Q |
| 43 | S | P | P |
| 44 | P | P | P |
| 45 | K | K | K |
| 46 | L | L | L |
| 47 | L | L | L |
| 48 | I | I | I |
| (L-FR2) 49 | Y | Y | Y |
| (L-CDR2) 50 | W | W | W |
| 51 | A | A | A |
| 52 | S | S | S |
| 53 | S | T | S |
| 54 | R | R | R |
| 55 | E | E | E |
| (L-CDR2) 56 | S | S | S |
| (L-FR3) 57 | G | G | G |
| 58 | V | V | V |
| 59 | P | P | P |
| 60 | D | D | D |
| 61 | R | R | R |
| 62 | F | F | F |
| 63 | T | S | S |
| 64 | G | G | G |
| 65 | S | S | S |
| 66 | G | G | G |
| 67 | S | S | S |
| 68 | G | G | G |
| 69 | T | T | T |
| 70 | D | D | D |
| 71 | F | F | F |
| 72 | T | T | T |
| 73 | L | L | L |
| 74 | T | T | T |
| 75 | I | I | I |
| 76 | S | S | S |
| 77 | S | S | S |
| 78 | V | L | L |
| 79 | K | Q | Q |
| 80 | T | A | A |
| 81 | E | E | E |
| 82 | D | D | D |
| 83 | L | V | V |
| 84 | A | A | A |
| 85 | V | V | V |
| 86 | Y | Y | Y |
| 87 | Y | Y | Y |
| (L-FR3) 88 | C | C | C |
| (L-CDR3) 89 | Q | Q | Q |
| 90 | Q | Q | Q |
| 91 | Y | Y | Y |
| 92 | F | Y | Y |
| 93 | S | S | S |
| 94 | Y | T | Y |
| 95 | P | P | P |
| 96 | F | | F |
| (L-CDR3) 97 | T | | T |
| (L-FR4) 98 | F | | F |
| 99 | G | | G |
| 100 | S | | Q |
| 101 | G | | G |
| 102 | T | | T |
| 103 | K | | K |
| 104 | L | | V |
| 105 | E | | E |
| 106 | I | | I |
| (L-FR4) 107 | K | | K |

The first column (Kabat & Chothia numbering) gives the residue number according to Kabat (Kabat et al. 1991) and Chothia (Al-Lazikani et al. 1997). FR and CDR identify the framework regions (L-FR1, L-FR2, L-FR3, and L-FR4) and the complementarity-determining regions (L-CDR1, L-CDR2, and L-CDR3) of the light chain variable domain, with the three CDRs separating the four FRs. The second column (mouse 280.46.3.4 VL) gives the amino acid sequence of the light chain variable domain of mouse 280.46.3.4. The third column (IGKV4-1) gives the amino acid sequence of human Immunoglobulin germline kappa variable gene 4-1 (accession number IMGT Z00023) used as human acceptor framework for CDR-grafting. The fourth column (Humanized 280.VK4-1-TSY) gives the amino acid sequence of the final optimized humanized version of mouse 280.46.3.4 VL; the residues underlined indicate the amino acids that differ from human germline IGKV4-1.

In order to eliminate the free cysteine, a second version of the humanized light chain, 280.VK4-1-S, recited in SEQ ID NO: 31, was designed and constructed where the cysteine was mutated to a serine which is the most conservative change possible in terms of the size and hydrophilicity. After protein A purification, the profile of the antibody without the cysteine (i.e. a humanized 280.46.3.4 antibody comprising 280.VH3-66-1 paired with 280.VK4-1-S), on an SDS gel (FIG. 5) looked better than the antibody containing the cysteine (i.e. a humanized 280.46.3.4 antibody comprising 280.VH3-66-1 paired with 280.VK4-1-C). By better profile it is meant that there is more correctly associated heavy and light chain than side products in the antibody without the unpaired cysteine (280.VK4-1-S; "After" in FIG. 5), as compared to the antibody containing the free cysteine (280.VK4-1-C; "Before" in FIG. 5).

Figure 6:
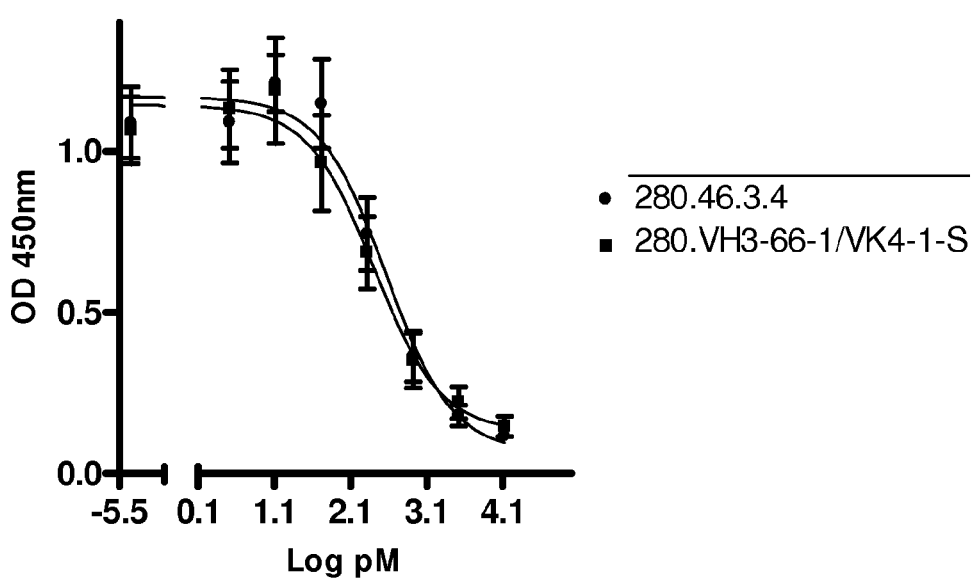
FIG. 6 reports the results of the STAT3 phosphorylation assay done in human HepG2 hepatoma cells to compare the potency of the humanized antibody expressed as a human IgG1/kappa, comprising 280.VH3-66-1 paired with 280.VK4-1-S (■ 280.VH3-66-1/VK4-1-S), with the mouse parental antibody 280.46.3.4 (● 280.46.3.4). The results show that the humanized antibody is 1.4 time more potent than the mouse parental antibody, which contains the free cysteine, with $IC_{50}$ values of 257.5 pM and 370.5 pM, respectively.

The potency of the humanized antibody expressed as a human IgG1/Kappa, comprising 280.VH3-66-1 paired with 280.VK4-1-S, was assessed in three distinct cellular assays:
1) STAT3 phosphorylation assay in human HepG2 hepatoma cells. The HepG2 human hepatoma cell line was obtained from ATCC (American Type Culture Collection) and stimulated with recombinant human IL-22 in 24-well plates. Serial dilutions of neutralizing antibodies were mixed with IL-22 at $EC_{80}$ and added to the cells for 20 min. HepG2 lysates were tested in PathScan Phospho-STAT3 Sandwich ELISA Kit from Cell Signaling to determine $IC_{50}$ values of tested antibodies. In this HepG2 assay, the humanized antibody was found to be 1.4 time more potent than the mouse parental antibody, which contains the free cysteine, purified from the 280.46.3.4 hybridoma (ATCC Patent Deposit Designation PTA-6284), with $IC_{50}$ values of 257.5 pM and 370.5 pM, respectively (FIG. 6).

Figure 7:
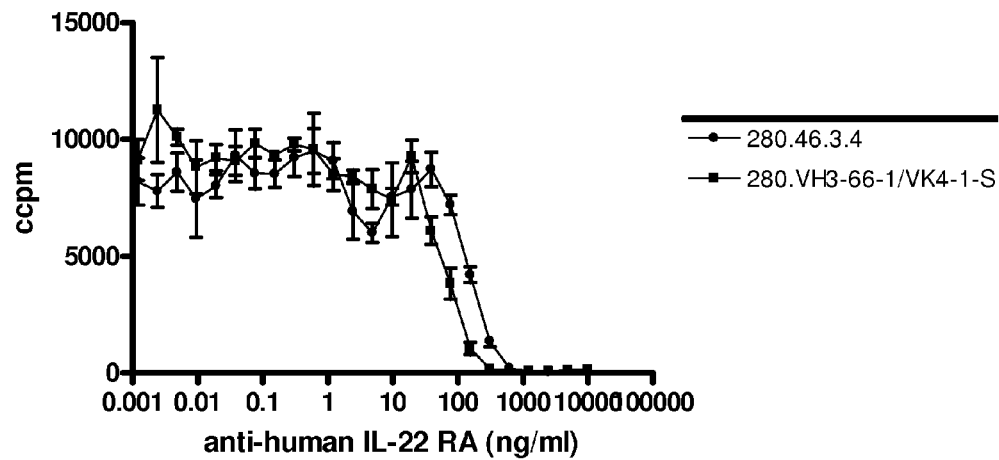
FIG. 7 reports the results of the proliferation assay done in human IL-22 receptor transfected-BaF3 stable cells to compare the potency of the humanized antibody expressed as a human IgG1/kappa, comprising 280.VH3-66-1 paired with 280.VK4-1-S (■ 280.VH3-66-1/VK4-1-S), with the mouse parental antibody 280.46.3.4 (● 280.46.3.4). The results show that the humanized antibody is 1.7 time more potent than the mouse parental antibody, which contains the free cysteine, with $IC_{50}$ values of 340 pM and 587 pM, respectively.

2) Proliferation assay in BaF3 cells. The BaF3 cell line was transfected with both human IL-22 receptor chains (IL-22RA and IL-10RB) and cultured with recombinant human IL-22 in 96-well plates. Serial dilutions of neutralizing antibodies were added to the cells and the effect on BaF3 proliferation was determined by tritiated thymidine incorporation measurement. In this human IL-22 receptor transfected-BaF3 stable cell line assay, the humanized antibody was found to be 1.7 time more potent than the mouse parental antibody, which contains the free cysteine, purified from the 280.46.3.4 hybridoma (ATCC Patent Deposit Designation PTA-6284), with $IC_{50}$ values of 340 and 587 pM, respectively (FIG. 7).

Figure 8:
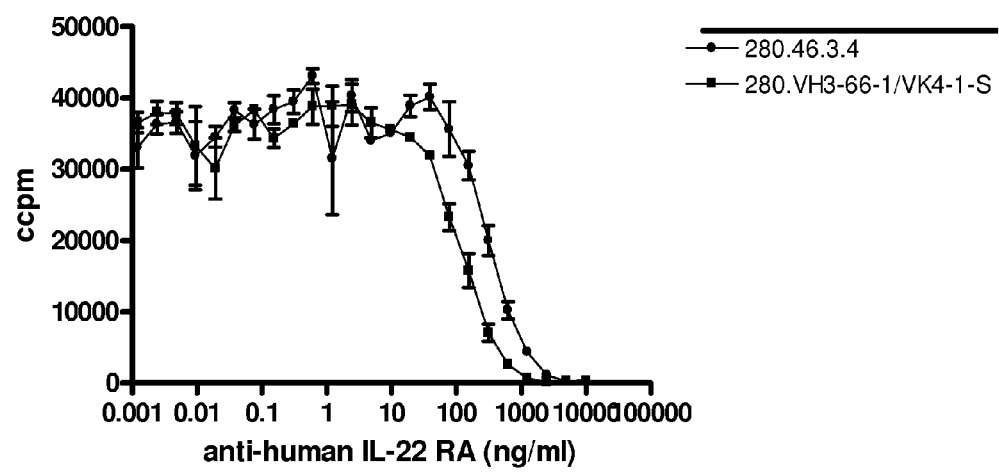
FIG. 8 reports the results of the proliferation assay done in murine IL-22 receptor transfected-BaF3 stable cells to compare the potency of the humanized antibody expressed as a human IgG1/kappa, comprising 280.VH3-66-1 paired with 280.VK4-1-S (■ 280.VH3-66-1/VK4-1-S), with the mouse parental antibody 280.46.3.4 (● 280.46.3.4). The results show that the humanized antibody is 2.1 times more potent than the mouse parental antibody, which contains the free cysteine, with $IC_{50}$ values of 693 pM and 1473 pM, respectively.

3) Proliferation assay in BaF3 cells. The BaF3 cell line was transfected with both murine IL22 receptor chains (IL-22RA and IL-10RB) and cultured with recombinant murine IL-22 in 96-well plates. Serial dilutions of neutralizing antibodies were added to the cells and the effect on BaF3 proliferation was determined by tritiated thymidine incorporation measurement. In this murine IL-22 receptor transfected-BaF3 stable cell line assay, the humanized antibody was found to be 2.1 time more potent than the mouse parental antibody, which contains the free cysteine, purified from the 280.46.3.4 hybridoma (ATCC Patent Deposit Designation PTA-6284), with $IC_{50}$ values of 693 and 1473 pM, respectively (FIG. 8).

In conclusion, the mutation of the free cysteine in the L-CDR1 has improved dramatically not only the biophysical properties but also the potency of the humanized 280.46.3.4 antibody comprising 280.VH3-66.1 paired with 280.VK4-1-S on both human and mouse IL-22RA, as compared to the original mouse 280.46.3.4 antibody.

Example 4

Removal of a Deamidation Motif in L-CDR1 and Increasing the Degree of Humanness in Humanized 280.46.3.4 VH Antibodies can be subject to a variety of chemical modification and/or degradation reactions for example deamidation, isomerization, hydrolysis, disulfide scrambling, beta-elimination, oxidation and adduct formation. The main hydrolytic mechanisms of degradation can include the deamidation of asparagines especially when immediately followed by a glycine or a serine. The substitution of the cysteine by a serine in the L-CDR1 has created an NS motif which constitutes a potential deamidation site and therefore should be eliminated. In an attempt to destroy this NS motif, a series of mutants was constructed (data not shown). It has been found that the best overall mutation was a change from the serine to a threonine. This mutated light chain variable domain (280.VK4-1-T), recited in SEQ ID NO: 32, was paired with the version 4 of the humanized 280.46.3.4 VH (280.VH3-66-4; see below) and assessed for inhibition potency in cell based assays.

In version 4 of the humanized 280.46.3.4 VH (280.VH3-66-4), residue 70 (Table 1) was mutated to the human germline residue found at this position, threonine to serine mutation. Also the last two residues of the H-CDR2, glutamic acid and alanine at position 64 and 65 (Table 1), were mutated to the human germline residues found at those positions; lysine and glycine respectively. Overall, version 4 of the humanized 280.46.3.4 VH (280.VH3-66-4), recited in SEQ ID NO: 33, has three more human germline residues as compared to version 1 (280.VH3-66-1) with two of these residues being located in H-CDR2 (FIG. 9 as compared to FIG. 4).

The potency of the humanized antibody expressed as a human IgG1/Kappa, comprising 280.VH3-66-4 paired with 280.VK4-1-T, was assessed in three distinct cellular assays as described above in Example 3:

1) In the HepG2 assay the humanized antibody was found to be 1.8 time more potent than the mouse parental antibody purified from the 280.46.3.4 hybridoma (ATCC Patent Deposit Designation PTA-6284), with $IC_{50}$ values of 183.2 and 333.0 pM, respectively (FIG. 10).

2) In the human IL-22 receptor transfected-BaF3 stable cell line assay, the humanized antibody was found to be 1.75 time more potent than the mouse parental antibody purified from the 280.46.3.4 hybridoma (ATCC Patent Deposit Designation PTA-6284), with $IC_{50}$ values of 334 and 587 pM, respectively (FIG. 11).

Figure 12:
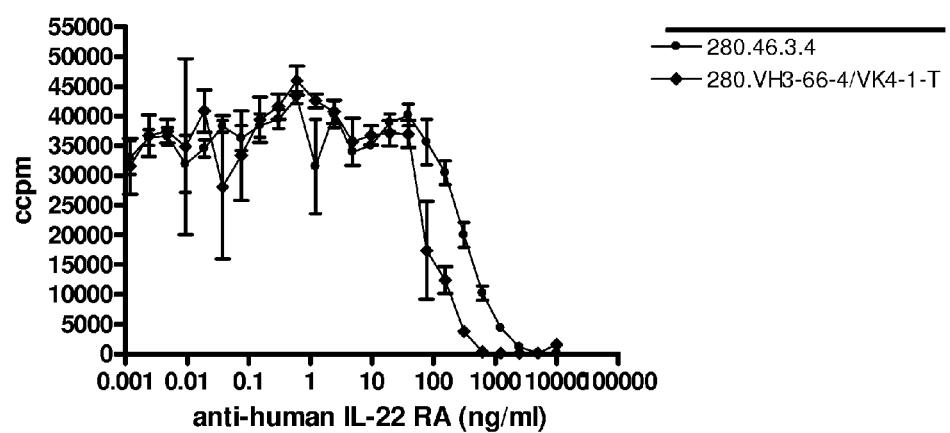
FIG. 12 reports the results of the proliferation assay done in murine IL-22 receptor transfected-BaF3 stable cells to compare the potency of the humanized antibody expressed as a human IgG1/kappa, comprising 280.VH3-66-4 paired with 280.VK4-1-T (♦ 280.VH3-66-4/VK4-1-T), with the mouse parental antibody 280.46.3.4 (● 280.46.3.4). The results show that the humanized antibody is 2.1 times more potent than the mouse parental antibody, with $IC_{50}$ values of 687 pM and 1473 pM, respectively.

3) In the murine IL-22 receptor transfected BaF3 stable cell line assay, the humanized antibody was found to be 2.1 times more potent than the mouse parental antibody purified from the 280.46.3.4 hybridoma (ATCC Patent Deposit Designation PTA-6284), with $IC_{50}$ values of 687 and 1473 pM, respectively (FIG. 12).

Example 5

Figure 13:
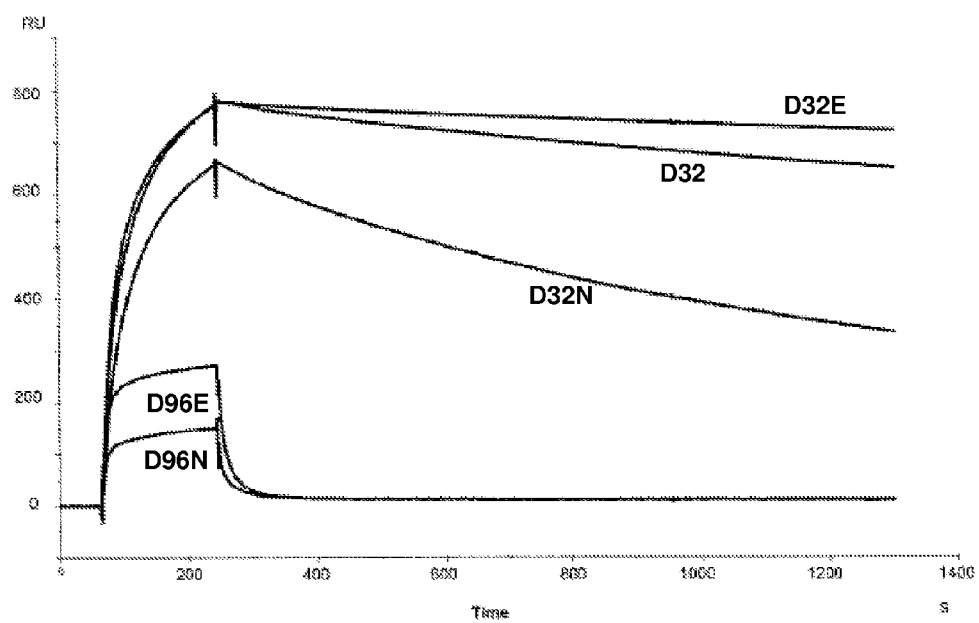
FIG. 13 reports the results of the Biacore analysis aiming at measuring the binding affinity to human IL-22RA of a set of mutants, where the Asp 32 in the H-CDR1 and Asp 96 in the H-CDR3 were individually mutated in 280.VH3-66-4. These single mutants were paired with the humanized light chain variable domain 280.VK4-1-T, and then tested for affinity measurement. D32E: mutation Asp to Glu at position 32 in 280.VH3-66-4 to create version 280.VH3-66-18; D32: parental version 280-VH3-66-4; D32N: mutation Asp to Asn at position 32 in 280.VH3-66-4; D96E: mutation Asp to Glu at position 96 in 280.VH3-66-4; D96N: mutation Asp to Asn at position 96 in 280.VH3-66-4. The results reported in this figure show that the D32E mutation increased the on rate by around 2 fold and decreased the off rate by about 5 fold as compared to the parental unmutated D32 (280.VH3-66-4). On the other hand, the D96E mutation had a negative impact, reducing the affinity by about 500 fold.
Figure 14:
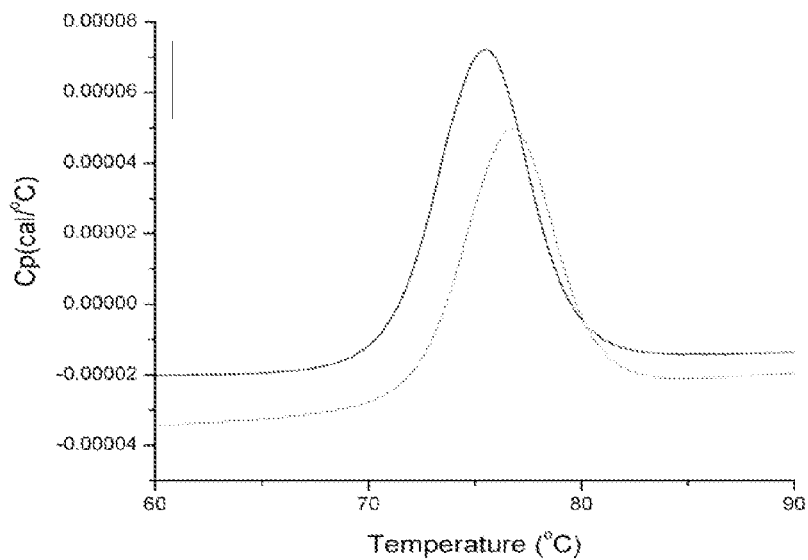
FIG. 14 reports the results of a differential scanning calorimetry (DSC) of the D32E mutant and of the parental unmutated D32 performed to examine their thermal stability. The D32E mutant (light grey line) is more stable by 1 degree than the parental D32 (dark grey line).

Mutation of Kabat Residue 32 from Asp to Glu in CDR1 of Humanized 280.46.3.4 VH Increase Affinity and Improves Stability Antibodies can be subject to a variety of chemical modification and/or degradation reactions for example deamidation, isomerization, hydrolysis, disulfide scrambling, beta-elimination, oxidation and adduct formation. The main hydrolytic mechanisms of degradation can include the isomerization of aspartic acid (Asp). In order to prevent this issue a set of mutants, where the Asp 32 in the H-CDR1 and Asp 96 in the H-CDR3 were individually mutated in 280.VH3-66-4, has been made. These single mutants were then paired with the humanized light chain variable domain 280.VK4-1-T, described above, and the resulting NiNTA-purified Fab antibody fragments tested for affinity measurement by Biacore. The VH containing the mutation Asp to Glu at position 32 in the H-CDR1 was called version 18 or 280.VH3-66-18 and is recited in SEQ ID NO: 34. The results of the Biacore analysis measuring the binding to human IL-22RA presented in FIG. 13 show that the D32E mutation increased the on rate by around 2 fold and decreased the off rate by about 5 fold as compared to the parental unmutated D32 (280.VH3-66-4). On the other hand, the D96E mutation had a negative impact, reducing the affinity by about 500 fold. The mutant D32E when analyzed by differential scanning calorimetry (DSC) appeared to be more stable by 1 degree than the parental D32 antibody (FIG. 14). Overall it can be concluded that the D32E mutation greatly improves the properties of the latest heavy chain humanized version 18 (280.VH3-66-18).

Figure 15:
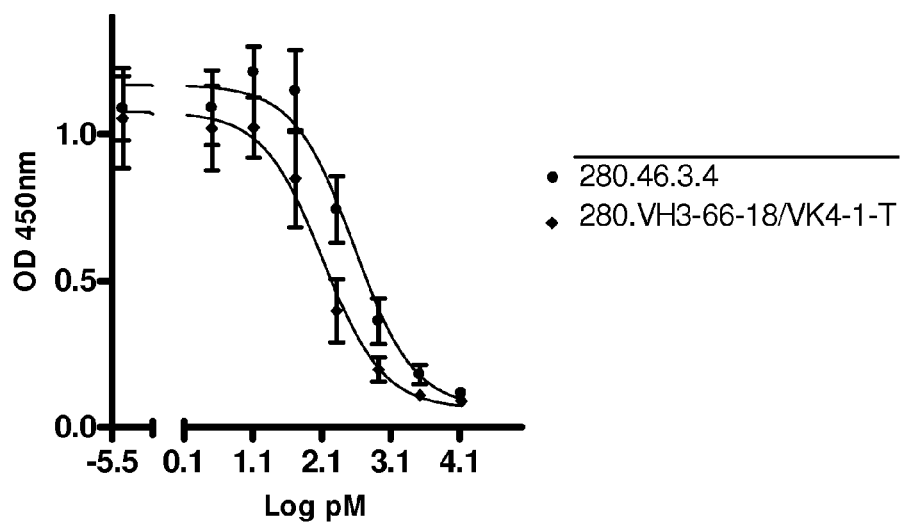
FIG. 15 reports the results of the STAT3 phosphorylation assay done in human HepG2 hepatoma cells to compare the potency of the humanized antibody expressed as a human IgG1/kappa, comprising 280.VH3-66-18 paired with 280.VK4-1-T (♦ 280.VH3-66-18/VK4-1-T), with the mouse parental antibody 280.46.3.4 (● 280.46.3.4). The results show that the humanized antibody is almost 3 times more potent than the mouse parental antibody, with $IC_{50}$ values of 132.5 pM and 370.5 pM, respectively.

The potency of the humanized antibody expressed as a human IgG1/Kappa, comprising 280.VH3-66.18 paired with 280.IGKV4-1-T, was assessed in a HepG2 cell assay. The results presented in FIG. 15 show that the humanized antibody (280.VH3-66.18/VK4-1-T) is almost 3 times more potent than the mouse parental antibody purified from the 280.46.3.4 hybridoma (ATCC Patent Deposit Designation PTA-6284), with $IC_{50}$ values of 132.5 and 370.5 pM, respectively.

Example 6

Increasing the Degree of Humanness

A. Heavy Chain

Having increased the affinity, the potency and the stability of the humanized 280.46.3.4 compared to the parental mouse 280.46.3.4, a series of mutants in an attempt to increase the humanness of the final humanized version has been designed. The aim was to mutate as many framework residues as possible that were of mouse parental origin back to the corresponding human germline IGHV3-66 residues. During this process the inventors were able to successfully back mutate residues Ala 67 and Leu 69 to residues Phe and Ile, respectively (Table 1). They also found that the introduction of an isoleucine at position 29, instead of the valine present in human germline IGHV3-66, had a positive impact on thermal stability (data not shown). Despite the fact that Ile 29 is not normally the residue found at this position in human germline IGHV3-66 (val 29) and because of its positive impact on stability with no loss of activity it has been decided to incorporate it in the final humanized VH version 46 (280.VH3-66-46), recited in SEQ ID NO. 16. The sequence alignment of the final humanized VH version, 280.VH3-66-46, with human germline IGHV3-66 shows that 9 mouse framework residues have been retained (FIG. 16 and Table 1).

B. Light Chain

In the humanized light chain, all framework residues being human, the possibility of germlining the CDR residues has been investigated. A series of mutants within mouse CDR residues were constructed by mutating individual CDR residues to the human germline IGKV4-1 residue found at the equivalent position. The mutants were screened by differential scanning calorimetry and Biacore to screen for thermal stability and affinity, respectively. It has been found that the Phe at position 92 in the L-CDR3 (Table 2) could be replaced by the Tyr residue present at this position in human germline IGKV4-1 with a gain of 1 degree Celsius in thermal stability and no loss in affinity. This optimized humanized VL sequence, named 280.VK4-1-TSY, is recited in SEQ ID NO. 17. Its alignment with the human germline IGKV4-1, shown in FIG. 17, indicates that 280.VK4-1-TSY has a very high identity with the whole germline IGKV4-1 sequence, including frameworks and CDR residues, since the sequences differ at only 5 positions (FIG. 17 and Table 2).

All the humanized antibodies mentioned above have been produced by linking the specific heavy chain variable domain to the constant region recited in SEQ ID NO: 18 and the specific light chain variable domain to the constant domain recited in SEQ ID NO: 19. It should be noted that these constant regions have been used as an example and can be easily replaced by different ones because the binding affinity and specificity of the antibodies reside in the variable domains. With respect to the above-cited Fabs, they comprise the first heavy chain constant domain ($CH_1$) of the sequence recited in SEQ ID NO: 18 and the light chain constant domain recited in SEQ ID NO: 19.

The different humanized antibodies and Fabs mentioned in the Examples have been produced in CHO cells using a single expression vector, which comprises the cDNAs coding for the heavy and light chain under the control of two different promoters.

Example 7

Potency of Humanized 280.VH3-66-46 VH Paired with 280.VK4-1-TSY VL in Human IL-22RA Expressing-Cell Assays The potency of the humanized antibody expressed as a human IgG1/Kappa, comprising 280.VH3-66.46 paired with 280.IGKV4-1-TSY, was assessed in three distinct cellular assays.

The term "280.346.TSY" is hereinafter used to indicate an anti-human IL-22RA humanized antibody comprising 280.VH3-66.46 paired with 280.IGKV4-1-TSY, irrespective of the heavy and light chain constant regions.

1) STAT3 phosphorylation assay in normal human keratinocytes. Normal human keratinocytes were obtained from Biopredic International and stimulated with recombinant human IL-22 in 96-well plates. Serial dilutions of neutralizing antibodies were mixed with IL-22 at $EC_{80}$ and added to the cells for 20 min. Keratinocyte lysates were tested in PathScan Phospho-STAT3 Sandwich ELISA Kit from Cell Signaling to determine $IC_{50}$ values of tested antibodies. In this normal human keratinocyte assay, 280.346.TSY was found to be almost 9 times more potent than the mouse parental antibody purified from the 280.46.3.4 hybridoma (ATCC Patent Deposit Designation PTA-6284), with $IC_{50}$ values of 60.95 and 541.9 pM, respectively (FIG. 18).

Figure 19:
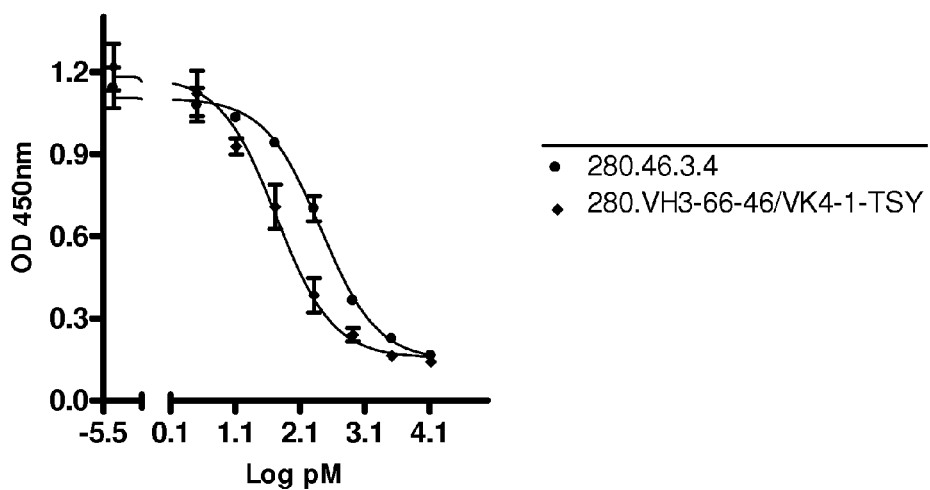
FIG. 19 reports the results of the STAT3 phosphorylation assay done in human HepG2 hepatoma cells to compare the potency of the humanized antibody expressed as a human IgG1/kappa, comprising 280.VH3-66-46 paired with 280.VK4-1-TSY (♦ 280.VH3-66-46/VK4-1-TSY), with the mouse parental antibody 280.46.3.4 (● 280.46.3.4). The results show that the humanized antibody (280.346.TSY, see Example 7) is almost 5 times more potent than the mouse parental antibody, with $IC_{50}$ values of 55.16 pM and 266.3 pM, respectively.

2) STAT3 phosphorylation assay in HepG2 cells. The HepG2 human hepatoma cell line was obtained from ATCC (American Type Culture Collection) and stimulated with recombinant human IL-22 in 24-well plates. Serial dilutions of neutralizing antibodies were mixed with IL-22 at $EC_{80}$ and added to the cells for 20 min. HepG2 lysates were tested in PathScan Phospho-STAT3 Sandwich ELISA Kit from Cell Signaling to determine $IC_{50}$ values of tested antibodies. In this HepG2 assay, 280.346.TSY was found to be almost 5 times more potent than the mouse parental antibody purified from the 280.46.3.4 hybridoma (ATCC Patent Deposit Designation PTA-6284), with $IC_{50}$ values of 55.16 and 266.3 pM, respectively (FIG. 19).

Figure 20:
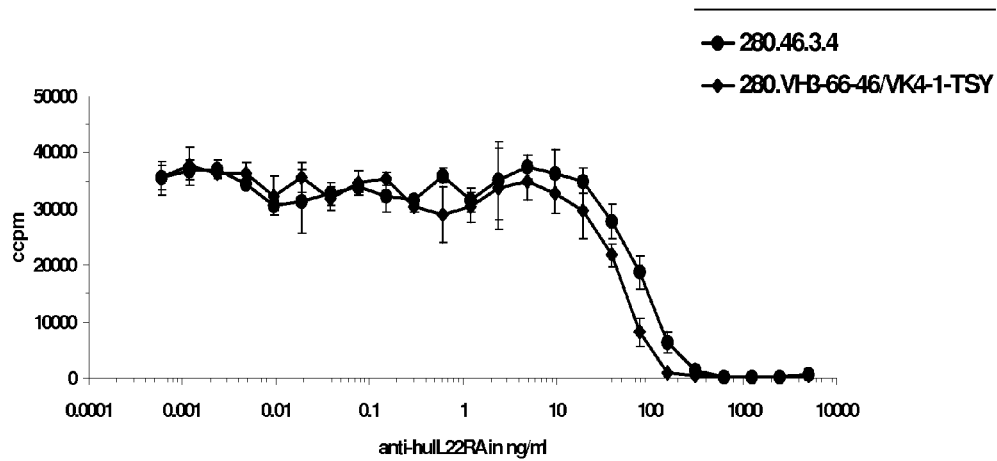
FIG. 20 reports the results of the proliferation assay done in human IL-22 receptor transfected-BaF3 stable cells to compare the potency of the humanized antibody expressed as a human IgG1/kappa, comprising 280.VH3-66-46 paired with 280.VK4-1-TSY (♦ 280.VH3-66-46/VK4-1-TSY), with the mouse parental antibody 280.46.3.4 (● 280.46.3.4). The results show that the humanized antibody (280.346.TSY, see Example 7) is 1.7 time more potent than the mouse parental antibody, with $IC_{50}$ values of 317 pM and 545 pM, respectively.

3) Proliferation assay in BaF3 cells. The BaF3 cell line was transfected with both human IL-22 receptor chains (IL-22RA and IL-10RB) and cultured with recombinant human IL-22 in 96-well plates. Serial dilutions of neutralizing antibodies were added to the cells and the effect on BaF3 proliferation was determined by tritiated thymidine incorporation measurement. In this human IL-22 receptor transfected-BaF3 stable cell line assay, 280.346.TSY was found to be 1.7 time more potent than the mouse parental antibody purified from the 280.46.3.4 hybridoma (ATCC Patent Deposit Designation PTA 6284), with $IC_{50}$ values of 317 and 545 pM, respectively (FIG. 20).

The amino acid sequence of the heavy and the light chain constant regions of a particular 280.346.TSY are recited in SEQ ID NO: 18 and 19 respectively, and the amino acid sequence of the entire heavy and light chain of said particular 280.346.TSY are recited in SEQ ID NO: 20 and 21, respectively.

Example 8

Potency of Humanized 280.346.TSY in Mouse IL-22RA Expressing-Cell Assays

Figure 21:
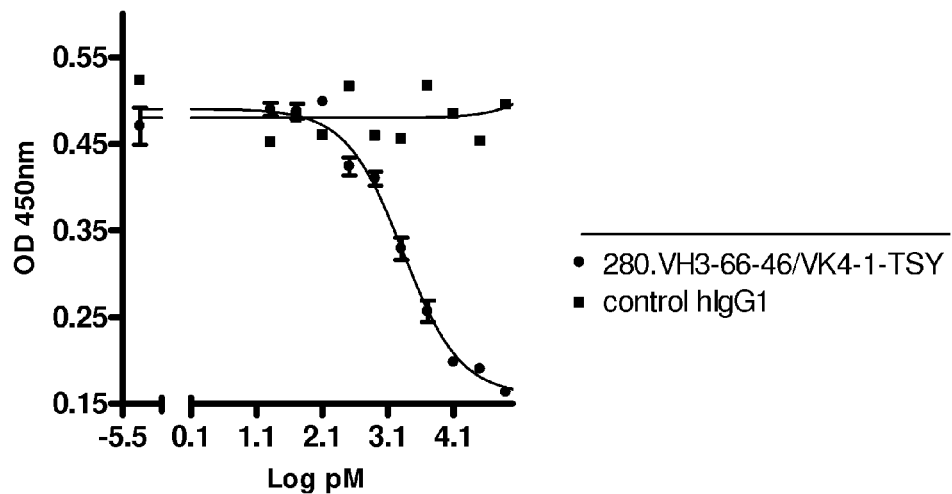
FIG. 21 reports the results of the STAT3 phosphorylation assay done in murine HEPA1-6 hepatoma cells to calculate the potency of the humanized antibody expressed as a human IgG1/kappa, comprising 280.VH3-66-46 paired with 280.VK4-1-TSY (● 280.VH3-66-46/VK4-1-TSY). A human IgG1 is used as a negative control (■ control hIgG1). The results show that the humanized antibody (280.346.TSY, see Example 7) is able to inhibit the activity of murine IL-22 with an $IC_{50}$ in the nanomolar range (2.1 nM).
Figure 22:
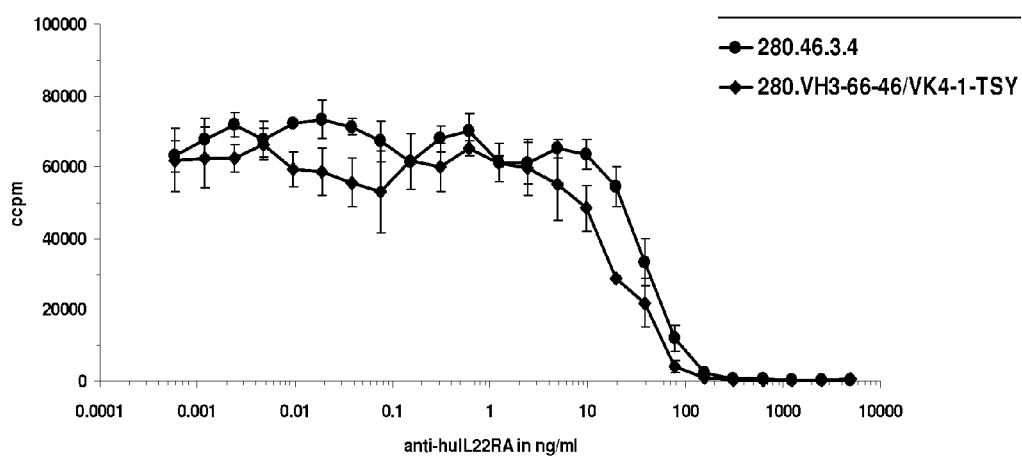
FIG. 22 reports the results of the proliferation assay done in murine IL-22 receptor transfected-BaF3 stable cells to compare the potency of the humanized antibody expressed as a human IgG1/kappa, comprising 280.VH3-66-46 paired with 280.VK4-1-TSY (♦ 280.VH3-66-46/VK4-1-TSY), with the mouse parental antibody 280.46.3.4 (● 280.46.3.4). The results show that the humanized antibody (280.346.TSY, see Example 7) is 6.2 times more potent than the mouse parental antibody, with $IC_{50}$ values of 137 pM and 849 pM, respectively.

The potency of 280.346.TSY was assessed in two distinct cellular assays:
1) STAT3 phosphorylation assay in HEPA1-6 cells. The HEPA1-6 murine hepatoma cell line was obtained from DSMZ (German Collection of Microorganisms and Cell Cultures) and stimulated with recombinant murine IL-22 in 96-well plates. Serial dilutions of neutralizing antibody were mixed with IL-22 at $EC_{80}$ and added to the cells for 20 min. A human IgG1 has been used as control. HEPA1-6 lysates were tested in PathScan Phospho-STAT3 Sandwich ELISA Kit from Cell Signaling to determine $IC_{50}$ values of tested antibodies. In this HEPA1-6 cell assay, 280.346.TSY was found to inhibit the activity of murine IL-22 with an $IC_{50}$ in the nanomolar range (2.1 nM; FIG. 21).
2) Proliferation assay in BaF3 cells. The BaF3 cell line was transfected with both murine IL-22 receptor chains (IL-22RA and IL-10RB) and cultured with recombinant murine IL-22 in 96-well plates. Serial dilutions of neutralizing antibodies were added to the cells and the effect on BaF3 proliferation was determined by tritiated thymidine incorporation measurement. In this mouse IL-22 receptor transfected-BaF3 stable cell line assay, 280.346.TSY was found to be 6.2 times more potent than the mouse parental antibody purified from the 280.46.3.4 hybridoma (ATCC Patent Deposit Designation PTA 6284), with $IC_{50}$ values of 137 and 849 pM, respectively (FIG. 22).

Example 9

Figure 23:
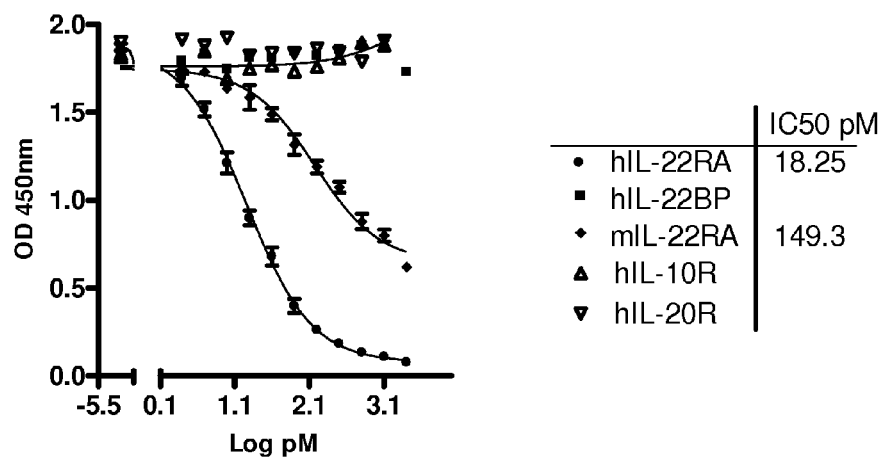
FIG. 23 reports the results of a competitive ELISA done to measure the specificity of 280.346.TSY to human IL-22RA. Microtiter plates were coated with human IL-22RA-ECD (i.e. IL-22RA-Extra Cellular Domain). Biotinylated 280-346-TSY antibody was added to the plate in the presence of competitors: human interleukin 22 receptor alpha (hIL-22RA), human IL-22 binding protein (hIL-22BP), murine IL-22 receptor alpha (mIL-22RA), human IL-10 receptor alpha (hIL-10R) and human IL-20 receptor alpha (hIL-20R). Binding to hIL-22RA coated on the plates is revealed by addition of peroxidase-conjugated streptavidin. Measured $IC_{50}$ values for human (● hIL-22RA) and murine (♦ mIL-22RA) IL-22RA are 18.25 pM and 149.3 pM respectively. 280.346.TSY does not show cross-reactivity with human IL-22BP (■ hIL-22BP), IL-10R alpha (ΔhIL-10R) and IL-20R alpha (∇ hIL-20R).

Binding Selectivity of 280.346.TSY on IL-22RA Related Proteins by Competitive ELISA Specificity and binding affinity of 280.346.TSY was determined using a competitive ELISA. Microtiter plates were coated with human IL-22RA-ECD (i.e. IL-22RA-Extra Cellular Domain). Biotinylated 280-346-TSY antibody was added to the plate in the presence of competitors: human interleukin 22 receptor alpha (hIL-22RA), human IL-22 binding protein (hIL-22BP), mouse IL-22 receptor alpha (mIL-22RA), human IL-10 receptor alpha (hIL-10R) and human IL-20 receptor alpha (hIL-20R). Binding to hIL-22RA coated on the plates was revealed by addition of peroxidase conjugated streptavidin. Measured $IC_{50}$ values for recombinant human and murine IL-22RA were 18.25 pM and 149.3 pM respectively (FIG. 23). Monoclonal antibody did not show cross-reactivity with recombinant human IL-22BP, IL-10R, and IL-20R.

Example 10

Cross Reactivity of 280-346-TSY Against IL-22RA Orthologues as Assessed by Kd Measurement by KinExA and Biacore The Kd of 280-346-TSY was assessed using both Biacore and KinExA instruments. The IL-22RA extracellular domains (ECD) of human and homologous gene sequences found in different species (rat, mouse, dog, rhesus monkey, cynomolgus monkey and marmoset monkey) were produced in HEK-293 cells and NiNTA-purified using a 6 His tag. The 280-346-TSY antibody has a subnanomolar affinity to human and all three monkey species of IL-22RA tested. It has a nanomolar affinity to mouse, with an affinity around a 100 times lower compared to human and a micromolar affinity to rat IL-22RA (Table 3).

TABLE 3

Kd affinity measurement of 280-346-TSY monoclonal antibody on human IL-22RA-ECD and its orthologues.

| IL-22RA-ECD | Kd KinExA | Kd Biacore |
|---|---|---|
| Human | ~28.5 pM | ~150 pM |
| Mouse | ~4.85 nM | ~20 nM |
| Rat | ~587 nM | ~1 µM |
| Rhesus | ~137 pM | ND |
| Cynomolgus | ~64.5 pM | ND |
| Marmoset | ~38.5 pM | 400 pM |
| Dog | Not Determined (ND) | 100 nM |

Example 11

Efficacy of 280-346-TSY on IL-22-Induced Serum Amyloid A in Mice

The pharmacodynamic activity of 280-346-TSY was determined on IL-22-induced serum amyloid A in male Balb/c mice. Different doses of 280.346.TSY were administered subcutaneously 22 hours prior to recombinant murine IL-22 intravenous injection. Vehicle control is PBS administered subcutaneously at 10 ml/kg.

Figure 24:
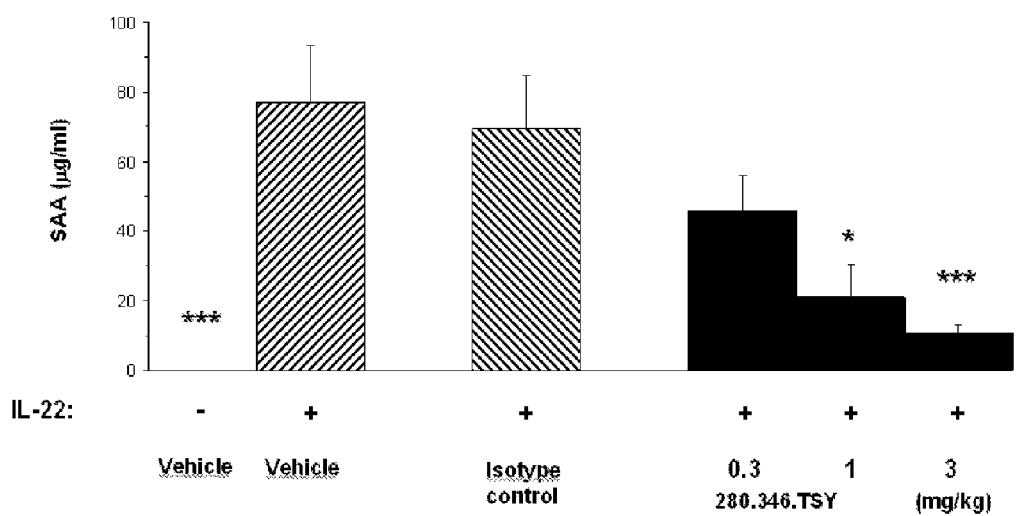
FIG. 24 reports the results of the pharmacodynamic activity of 280-346-TSY on IL-22-induced serum amyloid A in mice. Different doses of 280.346.TSY were administered subcutaneously 22 hours prior to recombinant murine IL-22 intravenous injection. Vehicle control is PBS administered subcutaneously. Blood sampling was performed 6 hours after IL-22 administration. A human IgG1 is used as a negative control (isotype control). Serum amyloid A was determined by ELISA. 280-346-TSY showed efficacy in this model and gave an $ED_{50}$ value of 0.5 mg/kg. Mann Whitney test was used to perform statistical analysis: * $p<0.05$ vs. isotype control group; *** $p<0.001$ vs. isotype control group.

Mice were given 100 µg/kg of IL-22 into the retroorbital plexus under isoflurane anesthesia. Blood sampling was performed 6 hours after IL-22 injection by cardiac puncture under isoflurane anesthesia. A human IgG1 was used as a negative control (isotype control). Serum amyloid A was determined by ELISA (Biosource). 280-346-TSY gave an $ED_{50}$ value of 0.5 mg/kg. Mann Whitney test was used to perform statistical analysis: * $p<0.05$ vs. isotype control group; *** $p<0.001$ vs. isotype control group (FIG. 24).

Example 12

Efficacy of 280-346-TSY on IL-23-Induced Ear Inflammation in Mice

The pharmacodynamic activity of 280-346-TSY was determined in a mouse model of psoriasis. Efficacy of 280-346-TSY on IL-23-induced ear thickening in female C57BL/6 mice was tested. Mice were injected with 500 ng of recombinant human IL-23 or PBS in a total volume of 20 µl every other day for 14 days as described by Zheng Y et al. (Nature 2007). Different doses of 280.346.TSY were administered subcutaneously every other day with the first dose given prior to first administration of recombinant IL-23.

Figure 25:
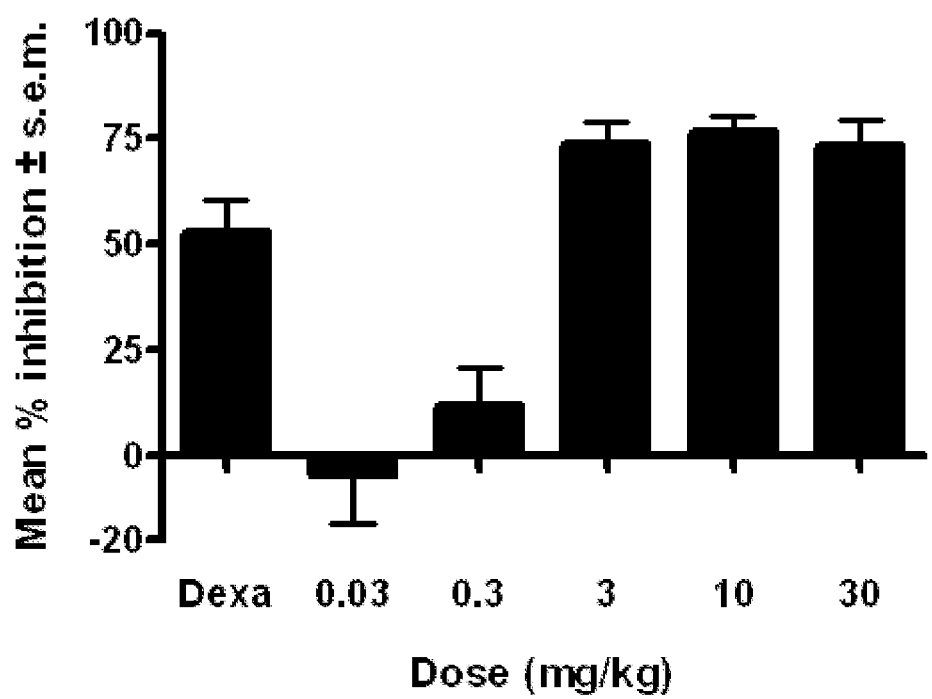
FIG. 25 reports the results of the pharmacodynamic activity of 280-346-TSY in a mouse model of psoriasis. Efficacy of 280-346-TSY on IL-23-induced ear thickening was determined. Mice were injected with 500 ng of recombinant human IL-23 or PBS every other day for 14 days. Full therapeutic coverage was performed with different doses of 280.346.TSY administered subcutaneously. Vehicle control is PBS administered subcutaneously. Dexamethasone (Dexa) is used as positive control. Percentage inhibition were calculated at day 9 which corresponds to the peak of ear swelling. 280-346-TSY showed efficacy in this model and gave an $ED_{50}$ value of 1.8 mg/kg.

Vehicle control is PBS administered subcutaneously at 10 ml/kg. Dexamethasone (Dexa) was used as positive control. Percentage inhibition were calculated at day 9 which corresponds to the peak of ear swelling. 280-346-TSY gave an $ED_{50}$ value of 1.8 mg/kg (FIG. 25).

| SEQ ID NO: | Sequence description |
|---|---|
| 1 | H-CDR1 (AEYMN) |
| 2 | H-CDR2 (EINPSTGTTTYNQKFKG) |
| 3 | H-CDR3 (FDAYFDY) |
| 4 | L-CDR1 (KSSQSLLYSSNQKNTLA) |
| 5 | L-CDR2 (WASSRES) |
| 6 | L-CDR3 (QQYYSYPFT) |
| 7 | Alternative L-CDR3 (QQYFSYPFT) |
| 8 | H-FR1 (EVQLVESGGGLVQPGGSLRLSCAASGYSIT) |
| 9 | H-FR2 (WVRQAPGKGLEWIG) |
| 10 | H-FR3 (RFTISVDQSKNTAYLQMNSLRAEDTAVYYCAR) |
| 11 | H-FR4 (WGQGTLVTVSS) |
| 12 | L-FR1 (DIVMTQSPDSLAVSLGERATINC) |
| 13 | L-FR2 (WYQQKPGQPPKLLIY) |
| 14 | L-FR3 (GVPDRFSGSGSGTDFTLTISSLQAEDVAVYYC) |
| 15 | L-FR4 (FGQGTKVEIKR) |
| 16 | Final humanized VH (280.VH3-66-46) |
| 17 | Final humanized VL (280.VK4-1-TSY) |
| 18 | Heavy chain constant region of a particular 280.346.TSY |
| 19 | Light chain constant domain of a particular 280.346.TSY |
| 20 | Heavy chain of a particular 280.346.TSY |
| 21 | Light chain of a particular 280.346.TSY |
| 22 | cDNA encoding the heavy chain of a particular 280.346.TSY |
| 23 | cDNA encoding the light chain of a particular 280.346.TSY |
| 24 | Amino acid sequence of human IL-22RA |
| 25 | Heavy chain variable domain of mouse 280.46.3.4 |
| 26 | Light chain variable domain of mouse 280.46.3.4 |
| 27 | Immunoglobulin kappa variable 4-1 (IGKV4-1) |
| 28 | Immunoglobulin heavy variable 3-66 (IGHV3-66) |
| 29 | First version of humanized 280.46.3.4 VL (280.VK4-1-C) |
| 30 | First version of humanized 280.46.3.4 VH (280.VH3-66.1) |
| 31 | Second version of humanized 280.46.3.4 VL (280.VK4-1-S) |
| 32 | Third version of humanized 280.46.3.4 VL (280.VK4-1-T) |
| 33 | Version 4 of the humanized 280.46.3.4 VH (280.VH3-66-4) |
| 34 | Version 18 of the humanized 280.46.3.4 VH (280.VH3-66-18) |

Reference List
1. Aggarwal S, Xie M H, Maruoka M, Foster J, Gurney A L. Acinar cells of the pancreas are a target of interleukin-22. J. Interferon Cytokine Res. 2001; 21: 1047-53.
2. Al-Lazikani B, Lesk A M, Chothia C. Standard conformations for the canonical structures of immunoglobulins. J Mol Biol. 1997; 273(4): 927-48.
3. Andoh A, Zhang Z, Inatomi O, Fujino S, Deguchi Y, Araki Y, Tsujikawa T, Kitoh K, Kim-Mitsuyama S, Takayanagi A et al. Interleukin-22, a member of the IL-10 subfamily, induces inflammatory responses in colonic subepithelial myofibroblasts. Gastroenterology 2005; 129: 969-84.
4. Aviv H and Leder P. Purification of biologically active globin messenger RNA by chromatography on oligothymidylic acid-cellulose. Proc Natl Acad Sci USA 1972; 69(6): 1408-12.
5. Chirgwin J M, Przybyla A E, MacDonald R J, Rutter W J. Isolation of biologically active ribonucleic acid from sources enriched in ribonuclease. Biochemistry 1979; 18(24): 5294-9.
6. Chothia C and Lesk A M. Canonical structures for the hypervariable regions of immunoglobulins. J. Mol. Biol. 1987; 196: 901-917.
7. Dumoutier L, Van Roost E, Colau D, Renauld JC. Human interleukin-10-related T cell-derived inducible factor: molecular cloning and functional characterization as a hepatocyte-stimulating factor. Proc. Natl. Acad. Sci. USA 2000; 97: 10144-49.
8. Francis G E, Fisher D, Delgado C, Malik F, Gardiner A, Neale D. PEGylation of cytokines and other therapeutic proteins and peptides: the importance of biological optimisation of coupling techniques. Int J Hematol. 1998; 68(1): 1-18.
9. Giudicelli V, Chaume D, Lefranc MP. IMGT/GENE-DB: a comprehensive database for human and mouse immunoglobulin and T cell receptor genes. Nucleic Acids Res. 2005; 33: D256-61.
10. Harris J M and Chess RB. Effect of pegylation on pharmaceuticals. Nat Rev Drug Discov. 2003; 2(3): 214-21.
11. Ikeuchi H, Kuroiwa T, Hiramatsu N, Kaneko Y, Hiromura K, Ueki K, Nojima Y. Expression of interleukin-22 in rheumatoid arthritis: potential role as a proinflammatory cytokine. Arthritis Rheum. 2005; 52: 1037-46.
12. Kabat et al. Sequences of Proteins of Immunological Interest. 5th Ed. Public Health Service, National Institutes of Health, Bethesda, Md. 1991
13. Kotenko S V, Izotova L S, Mirochnitchenko O V, Esterova E, Dickensheets H, Donnelly R P, Pestka S. Identification, cloning, and characterization of a novel soluble receptor that binds IL-22 and neutralizes its activity. J Immunol. 2001; 166: 7096-7103.
14. Kunz S, Wolk K, Witte E, Witte K, Doecke W D, Volk H D, Sterry W, Asadullah K, Sabat R. Interleukin (IL)-19, IL-20 and IL-24 are produced by and act on keratinocytes and are distinct from classical ILs. Experimental Dermatology 2006; 15: 991-1004.
15. Langer J A, Cutrone E C, Kotenko S. The Class II cytokine receptor (CRF2) family: overview and patterns of receptor-ligand interactions. Cytokine & Growth Factor Review 2004; 15: 33-48.
16. Li J, Tomkinson K N, Tan X, Wu P et al. Temporal associations between interleukin 22 and the extracellular domains of IL-22R and IL-10R2. Int Immunopharmacol. 2004; 4(5):693-708.
17. Moore K W, de Waal Malefyt R, Coffman R L, O'Garra A. Interleukin-10 and the interleukin-10 receptor. Annu. Rev. Immunol. 2001; 19: 683-765.
18. Nograles K E, Brasington R D, Bowcock A M. New insights into the pathogenesis and genetics of psoriatic arthritis. Nat Clin Pract Rheumatol. 2009a; 5(2): 83-91.
19. Nograles K E, Zaba L C, Shemer A, Fuentes-Duculan J, Cardinale I, Kikuchi T, Ramon M, Bergman R, Krueger J G, Guttman-Yassky E. IL-22-producing "T22" T cells account for upregulated IL-22 in atopic dermatitis despite reduced IL-17-producing TH17 T cells. J Allergy Clin Immunol. 2009b; 123(6): 1244-52.
20. Wolk K, Kunz S, Witte E, Friedrich M, Asadullah K, Sabat R. IL-22 increases the innate immunity of tissues. Immunity 2004; 21: 241-54.
21. Zheng Y, Danilenko D M, Valdez P, Kasman I, Eastham-Anderson J, Wu J, Ouyang W. Interleukin-22, a T(H)17 cytokine, mediates IL-23-induced dermal inflammation and acanthosis. Nature 2007; 445: 648-51.
22. WO 2006/047249
23. WO 99/07848

The invention claimed is:

1. A humanized antibody that binds to human interleukin-22 receptor alpha (IL-22RA) wherein said humanized antibody comprises:
   a) a heavy chain variable domain comprising H-CDR1, H-CDR2, and H-CDR3, said H-CDR1, H-CDR2, and H-CDR3 consisting of amino acid sequences of SEQ ID NOs: 1, 2 and 3, respectively; and
   b) a light chain variable domain comprising L-CDR1, L-CDR2, and L-CDR3, said L-CDR1, L-CDR2, and L-CDR3 consisting of amino acid sequences of SEQ ID NOs: 4, 5, and 6, respectively, or consisting of amino acid sequences of SEQ ID NOs: 4, 5 and 7, respectively.

2. The humanized antibody according to claim 1, wherein:
   a) said heavy chain variable domain comprises framework regions H-FR1, H-FR2, H-FR3 and H-FR4, said framework regions consisting of amino acid sequences of SEQ ID NOs: 8, 9, 10 and 11, respectively; and
   b) said light chain variable domain comprises framework regions L-FR1, L-FR2, L-FR3 and L-FR4, said framework regions consisting of amino acid sequences of SEQ ID NOs: 12, 13, 14, and 15, respectively.

3. The humanized antibody according to claim 1, wherein:
   a) said heavy chain variable domain consists of the amino acid sequence of SEQ ID NO: 16; and
   b) said light chain variable domain consists of the amino acid sequence of SEQ ID NO: 17.

4. The humanized antibody according to claim 1, wherein said antibody comprises:
   a) a heavy chain constant region consisting of the amino acid sequence of SEQ ID NO: 18; and
   b) a light chain constant domain consisting of the amino acid sequence of SEQ ID NO: 19.

5. The humanized antibody of claim 1, wherein said antibody comprises:
   a) a heavy chain variable domain comprising H-CDR1, H-CDR2, and H-CDR3 consisting of amino acid sequences of SEQ ID NOs: 1, 2 and 3, respectively; and
   b) a light chain variable domain comprising L-CDR1, L-CDR2, and L-CDR3, said L-CDR1, L-CDR2, and L-CDR3 consisting of amino acid sequences of SEQ ID NOs: 4, 5 and 6.

6. The humanized antibody of claim 1, wherein said antibody comprises:
   a) a heavy chain variable domain comprising H-CDR1, H-CDR2, and H-CDR3, said H-CDR1, H-CDR2, and H-CDR3 consisting of amino acid sequences of SEQ ID NOs: 1, 2 and 3, respectively; and
   b) a light chain variable domain comprising L-CDR1, L-CDR2, and L-CDR3, said L-CDR1, L-CDR2, and L-CDR3 consisting of amino acid sequences of SEQ ID NOs: 4, 5 and 7, respectively.

7. A humanized antibody that binds to human interleukin-22 receptor alpha (IL-22RA), said humanized antibody:
   a) comprising a heavy chain comprising the amino acid sequence of SEQ ID NO: 20 and a light chain comprising the amino acid sequence of SEQ ID NO: 21; or
   b) comprising a heavy chain consisting of the amino acid sequence of SEQ ID NO: 20 and a light chain consisting of the amino acid sequence of SEQ ID NO: 21.

8. A polynucleotide encoding the heavy chain and/or the light a chain of a humanized antibody:
   a) comprising a heavy chain comprising the amino acid sequence of SEQ II NO: 20 and a light chain comprising the amino acid sequence of SEQ ID NO: 21; or
   b) comprising a heavy chain consisting the amino acid sequence of SEQ ID NO: 20 and a light chain consisting of the amino acid sequence of SEQ ID NO: 21.

9. The polynucleotide according to claim 8, wherein said polynucleotide comprises the amino acid sequence of SEQ ID NO: 22.

10. The polynucleotide according to claim 8, wherein said polynucleotide comprises the amino acid sequence of SEQ ID NO: 23.

11. An expression vector comprising a polynucleotide encoding the heavy chain and/or the light chain of a humanized antibody:
   a) comprising a heavy chain comprising the amino acid sequence of SEQ ID NO: 20 and a light chain comprising the amino acid sequence of SEQ ID NO: 21; or
   b) comprising a heavy chain consisting of the amino acid sequence of SEQ ID NO: 20 and a light chain consisting of the amino acid sequence of SEQ ID NO): 21.

12. A host cell transformed with an expression vector encoding the heavy chain and/or the light chain of a humanized antibody:
   a) comprising a heavy chain comprising the amino acid sequence of SEQ ID NO: 20 and a light chain comprising the amino acid sequence of SEQ ID NO: 21 ; or
   b) comprising a heavy chain consisting of the amino acid sequence of SEQ ID NO: 20 and a light chain consisting of the amino acid sequence of SEQ ID NO: 21.

13. The host cell according to claim 12, wherein said cell is a Chinese hamster ovary (CHO) cell.

14. The host cell according to claim 12, wherein said host cell is an isolated host cell.

15. A method of producing a humanized antibody comprising culturing a host cell transformed with an expression vector encoding the heavy chain and/or the light chain of a humanized antibody:
   a) comprising a heavy chain comprising the amino acid sequence of SEQ ID NO: 20 and a light chain comprising the amino acid sequence of SEQ ID NO: 21; or
   b) comprising a heavy chain consisting of the amino acid sequence of SEQ ID NO: 20 and a light chain consisting of the amino acid sequence of SE ID NO: 21.

16. A pharmaceutical composition comprising wherein said humanized antibody that binds to human interleukin-22 receptor alpha (IL-22RA) wherein said humanized antibody comprises:
   a) a heavy chain variable domain comprising H-CDR1, H-CDR2, and H-CDR3, said H-CDR1, H-CDR2, and H-CDR3 consisting of amino acid sequences of SEQ ID NOs: 1, 2 and 3, respectively; and
   b) a light chain variable domain comprising L-CDR1, L-CDR2, and L-CDR3, said L-CDR1, L-CDR2, and L-CDR3 consisting of amino acid sequences of SEQ ID NOs: 4, 5, and 6, respectively, or consisting of amino acid sequences of SEQ ID NOs: 4, 5 and 7, respectively.

17. A method of treating psoriasis, psoriatic arthritis or atopic dermatitis comprising the administration of a therapeutically effective amount of a humanized antibody that binds to human interleukin-22 receptor alpha (IL-22RA) wherein said humanized antibody comprises:
   a) a heavy chain variable domain comprising H-CDR1, H-CDR2 and H-CDR3, said H-CDR1 H-CDR2, and H-CDR3 consisting of amino acid sequences of SEQ ID NOs: 1, 2 and 3, respectively; and b) a light chain variable domain comprising L-CDR1, L-CDR2, and L-CDR3, said L-CDR1, L-CDR2 . and L-CDR3 consisting of amino acid sequences of SEQ ID NOs: 4, 5 and 6, respectively, or consisting of amino acid sequences of SEQ ID NOs: 4, 5 and 7, respectively.

18. The method of claim 17, wherein said humanized antibody that binds to human interleukin-22 receptor alpha (IL-22RA) comprises:
   a) a heavy chain variable domain comprising H-CDR1, H-CDR2, and H-CDR3, said H-CDR1, H-CDR2, and H-CDR3 consisting of amino acid sequences of SEQ ID NOs: 1, 2 and 3, respectively; and
   b) a light chain variable domain comprising L-CDR1, L-CDR2, and L-CDR3, said L-CDR1, L-CDR2 . and L-CDR3 consisting of amino acid sequences of SEQ ID NOs: 4, 5 and 6.

19. The method of claim 17, wherein said humanized antibody that binds to human interleukin-22 receptor alpha (IL-22RA) which comprises:
   a) a heavy chain variable domain comprising H-CDR1, H-CDR2, and H-CDR3, said H-CDR1, H-CDR2, and H-CDR3 consisting of amino acid sequences of SEQ ID NOs: 1, 2 and 3, respectively; and
   b) a light chain variable domain comprising L-CDR1, L-CDR2, and L-CDR3, said L-CDR1, L-CDR2, and L-CDR3 consisting of amino acid sequences of SEQ ID NOs: 4, 5 and 7, respectively.

\* \* \* \* \*

UNITED STATES PATENT AND TRADEMARK OFFICE
CERTIFICATE OF CORRECTION

PATENT NO. : 8,545,844 B2  
APPLICATION NO. : 13/510068  
DATED : October 1, 2013  
INVENTOR(S) : Roland Beckmann and Caroline Johnson-Leger Page 1 of 1

It is certified that error appears in the above-identified patent and that said Letters Patent is hereby corrected as shown below:

Title Page,
(73) Assignee, "Merck Serona SA, Coinsins, Vaud (CH)" should read
--Merck Serono SA, Coinsins, Vaud (CH)--.

In the Specifications,
Column 7,
Line 67, "p and E" should read --$\mu$ and $\varepsilon$--.

Column 9,
Line 39, "of heavy" should read --of a heavy--.

In the Claims,
Column 60, Claim 8,
Line 35, "SEQ II NO: 20" should read --SEQ ID NO: 20--.

Signed and Sealed this
Fourth Day of March, 2014

Michelle K. Lee
*Deputy Director of the United States Patent and Trademark Office*

SEQUENCE LISTING

<160> NUMBER OF SEQ ID NOS: 37

<210> SEQ ID NO 1
<211> LENGTH: 5
<212> TYPE: PRT
<213> ORGANISM: Artificial
<220> FEATURE:
<223> OTHER INFORMATION: H-CDR1

<400> SEQUENCE: 1

Ala Glu Tyr Met Asn
1               5

<210> SEQ ID NO 2
<211> LENGTH: 17
<212> TYPE: PRT
<213> ORGANISM: Artificial
<220> FEATURE:
<223> OTHER INFORMATION: H-CDR2

<400> SEQUENCE: 2

Glu Ile Asn Pro Ser Gly Thr Thr Thr Tyr Asn Gln Lys Phe Lys
1               5                   10                  15

Gly

<210> SEQ ID NO 3
<211> LENGTH: 7
<212> TYPE: PRT
<213> ORGANISM: Artificial
<220> FEATURE:
<223> OTHER INFORMATION: H-CDR3

<400> SEQUENCE: 3

Phe Asp Ala Tyr Phe Asp Tyr
1               5

<210> SEQ ID NO 4
<211> LENGTH: 17
<212> TYPE: PRT
<213> ORGANISM: Artificial
<220> FEATURE:
<223> OTHER INFORMATION: L-CDR1

<400> SEQUENCE: 4

Lys Ser Ser Gln Ser Leu Leu Tyr Ser Ser Asn Gln Lys Asn Thr Leu
1               5                   10                  15

Ala

<210> SEQ ID NO 5
<211> LENGTH: 7
<212> TYPE: PRT
<213> ORGANISM: Artificial
<220> FEATURE:
<223> OTHER INFORMATION: L-CDR2

<400> SEQUENCE: 5

Trp Ala Ser Ser Arg Glu Ser
1               5

<210> SEQ ID NO 6
<211> LENGTH: 9
<212> TYPE: PRT
<213> ORGANISM: Artificial
<220> FEATURE:
<223> OTHER INFORMATION: L-CDR3

<400> SEQUENCE: 6

Gln Gln Tyr Tyr Ser Tyr Pro Phe Thr
1               5

<210> SEQ ID NO 7
<211> LENGTH: 9
<212> TYPE: PRT
<213> ORGANISM: Artificial
<220> FEATURE:
<223> OTHER INFORMATION: Alternative L-CDR3

<400> SEQUENCE: 7

Gln Gln Tyr Phe Ser Tyr Pro Phe Thr
1               5

<210> SEQ ID NO 8
<211> LENGTH: 30
<212> TYPE: PRT
<213> ORGANISM: Artificial
<220> FEATURE:
<223> OTHER INFORMATION: H-FR1

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Ser Ile Thr
            20                  25                  30

<210> SEQ ID NO 9
<211> LENGTH: 14
<212> TYPE: PRT
<213> ORGANISM: Artificial
<220> FEATURE:
<223> OTHER INFORMATION: H-FR2

<400> SEQUENCE: 9

Trp Val Arg Gln Ala Pro Gly Lys Gly Leu Glu Trp Ile Gly
1               5                   10

<210> SEQ ID NO 10
<211> LENGTH: 32
<212> TYPE: PRT
<213> ORGANISM: Artificial
<220> FEATURE:
<223> OTHER INFORMATION: H-FR3

<400> SEQUENCE: 10

Arg Phe Thr Ile Ser Val Asp Gln Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 11
<211> LENGTH: 11
<212> TYPE: PRT
<213> ORGANISM: Artificial
<220> FEATURE:
<223> OTHER INFORMATION: H-FR4

<400> SEQUENCE: 11

Trp Gly Gln Gly Thr Leu Val Thr Val Ser Ser
1               5                   10

<210> SEQ ID NO 12
<211> LENGTH: 23

```
<212> TYPE: PRT
<213> ORGANISM: Artificial
<220> FEATURE:
<223> OTHER INFORMATION: L-FR1

<400> SEQUENCE: 12

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 13
<211> LENGTH: 15
<212> TYPE: PRT
<213> ORGANISM: Artificial
<220> FEATURE:
<223> OTHER INFORMATION: L-FR2

<400> SEQUENCE: 13

Trp Tyr Gln Gln Lys Pro Gly Gln Pro Pro Lys Leu Leu Ile Tyr
1               5                   10                  15

<210> SEQ ID NO 14
<211> LENGTH: 32
<212> TYPE: PRT
<213> ORGANISM: Artificial
<220> FEATURE:
<223> OTHER INFORMATION: L-FR3

<400> SEQUENCE: 14

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 15
<211> LENGTH: 11
<212> TYPE: PRT
<213> ORGANISM: Artificial
<220> FEATURE:
<223> OTHER INFORMATION: L-FR4

<400> SEQUENCE: 15

Phe Gly Gln Gly Thr Lys Val Glu Ile Lys Arg
1               5                   10

<210> SEQ ID NO 16
<211> LENGTH: 116
<212> TYPE: PRT
<213> ORGANISM: Artificial
<220> FEATURE:
<223> OTHER INFORMATION: Final humanized VH (280.VH3-66-46)
<220> FEATURE:
<221> NAME/KEY: BINDING
<222> LOCATION: (31)..(35)
<223> OTHER INFORMATION: H-CDR1 (i.e. SEQ ID NO: 1)
<220> FEATURE:
<221> NAME/KEY: BINDING
<222> LOCATION: (50)..(66)
<223> OTHER INFORMATION: H-CDR2 (i.e. SEQ ID NO: 2)
<220> FEATURE:
<221> NAME/KEY: BINDING
<222> LOCATION: (99)..(105)
<223> OTHER INFORMATION: H-CDR3 (i.e. SEQ ID NO: 3)

<400> SEQUENCE: 16

Glu Val Gln Leu Val Glu Ser Gly Gly Gly Leu Val Gln Pro Gly Gly
1               5                   10                  15
```

-continued

```
Ser Leu Arg Leu Ser Cys Ala Ala Ser Gly Tyr Ser Ile Thr Ala Glu
            20                  25                  30

Tyr Met Asn Trp Val Arg Gln Ala Pro Gly Lys Gly Leu Glu Trp Ile
        35                  40                  45

Gly Glu Ile Asn Pro Ser Thr Gly Thr Thr Tyr Asn Gln Lys Phe
50                  55                  60

Lys Gly Arg Phe Thr Ile Ser Val Asp Gln Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Phe Asp Ala Tyr Phe Asp Tyr Trp Gly Gln Gly Thr Leu Val
            100                 105                 110

Thr Val Ser Ser
        115

<210> SEQ ID NO 17
<211> LENGTH: 114
<212> TYPE: PRT
<213> ORGANISM: Artificial
<220> FEATURE:
<223> OTHER INFORMATION: Final humanized VL (280.VK4-1-TSY)
<220> FEATURE:
<221> NAME/KEY: BINDING
<222> LOCATION: (24)..(40)
<223> OTHER INFORMATION: L-CDR1 (i.e. SEQ ID NO: 4)
<220> FEATURE:
<221> NAME/KEY: BINDING
<222> LOCATION: (56)..(62)
<223> OTHER INFORMATION: L-CDR2 (i.e. SEQ ID NO: 5)
<220> FEATURE:
<221> NAME/KEY: BINDING
<222> LOCATION: (95)..(103)
<223> OTHER INFORMATION: L-CDR2 (i.e. SEQ ID NO: 6)

<400> SEQUENCE: 17

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Thr Leu Ala Trp Tyr Gln Gln Lys Pro Gly Gln
        35                  40                  45

Pro Pro Lys Leu Leu Ile Tyr Trp Ala Ser Ser Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Phe Thr Phe Gly Gln Gly Thr Lys Val Glu Ile
            100                 105                 110

Lys Arg

<210> SEQ ID NO 18
<211> LENGTH: 329
<212> TYPE: PRT
<213> ORGANISM: Artificial
<220> FEATURE:
<223> OTHER INFORMATION: Heavy chain constant region of a particular
      280.346.TSY

<400> SEQUENCE: 18

Ala Ser Thr Lys Gly Pro Ser Val Phe Pro Leu Ala Pro Ser Ser Lys
1               5                   10                  15
```

-continued

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Lys Phe Asn Trp Tyr
145                 150                 155                 160

Val Asp Gly Val Glu Val His Asn Ala Lys Thr Lys Pro Arg Glu Glu
                165                 170                 175

Gln Tyr Asn Ser Thr Tyr Arg Val Val Ser Val Leu Thr Val Leu His
            180                 185                 190

Gln Asp Trp Leu Asn Gly Lys Glu Tyr Lys Cys Lys Val Ser Asn Lys
        195                 200                 205

Ala Leu Pro Ser Ser Ile Glu Lys Thr Ile Ser Lys Ala Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Val Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 19
<211> LENGTH: 106
<212> TYPE: PRT
<213> ORGANISM: Artificial
<220> FEATURE:
<223> OTHER INFORMATION: Light chain constant domain of a particular
      280.346.TSY

<400> SEQUENCE: 19

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

```
Gly Asn Ser Gln Glu Ser Val Thr Glu Gln Asp Ser Lys Asp Ser Thr
         50                  55                  60

Tyr Ser Leu Ser Ser Thr Leu Thr Leu Ser Lys Ala Asp Tyr Glu Lys
 65                  70                  75                  80

His Lys Val Tyr Ala Cys Glu Val Thr His Gln Gly Leu Ser Ser Pro
                 85                  90                  95

Val Thr Lys Ser Phe Asn Arg Gly Glu Cys
            100                 105

<210> SEQ ID NO 20
<211> LENGTH: 445
<212> TYPE: PRT
<213> ORGANISM: Artificial
<220> FEATURE:
<223> OTHER INFORMATION: Heavy chain of a particular 280.346.TSY
<220> FEATURE:
<221> NAME/KEY: DOMAIN
<222> LOCATION: (1)..(116)
<223> OTHER INFORMATION: Heavy chain variable domain (i.e. SEQ ID NO:
      16)
<220> FEATURE:
<221> NAME/KEY: MISC_FEATURE
<222> LOCATION: (117)..(445)
<223> OTHER INFORMATION: Heavy chain constant region (i.e. SEQ ID NO:
      18)

<400> SEQUENCE: 20

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Ile Thr Ala Glu
             20                  25                  30

Tyr Met Asn Trp Val Arg Gln Ala Pro Gly Lys Gly Leu Glu Trp Ile
         35                  40                  45

Gly Glu Ile Asn Pro Ser Thr Gly Thr Thr Tyr Asn Gln Lys Phe
     50                  55                  60

Lys Gly Arg Phe Thr Ile Ser Val Asp Gln Ser Lys Asn Thr Ala Tyr
 65                  70                  75                  80

Leu Gln Met Asn Ser Leu Arg Ala Glu Asp Thr Ala Val Tyr Tyr Cys
                 85                  90                  95

Ala Arg Phe Asp Ala Tyr Phe Asp Tyr Trp Gly Gln Gly Thr Leu Val
                100                 105                 110

Thr Val Ser Ser Ala Ser Thr Lys Gly Pro Ser Val Phe Pro Leu Ala
            115                 120                 125

Pro Ser Ser Lys Ser Thr Ser Gly Gly Thr Ala Ala Leu Gly Cys Leu
        130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Arg Val Glu Pro Lys Ser Cys Asp Lys Thr His Thr
    210                 215                 220

Cys Pro Pro Cys Pro Ala Pro Pro Val Ala Gly Pro Ser Val Phe Leu
225                 230                 235                 240

Phe Pro Pro Lys Pro Lys Asp Thr Leu Met Ile Ser Arg Thr Pro Glu
                245                 250                 255
```

```
Val Thr Cys Val Val Asp Val Ser His Glu Asp Pro Glu Val Lys
                260                 265                 270

Phe Asn Trp Tyr Val Asp Gly Val Glu Val His Asn Ala Lys Thr Lys
            275                 280                 285

Pro Arg Glu Glu Gln Tyr Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Ala Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Glu Glu Met Thr Lys Asn Gln Val Ser Leu Thr Cys Leu Val Lys
355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys
435                 440                 445

<210> SEQ ID NO 21
<211> LENGTH: 220
<212> TYPE: PRT
<213> ORGANISM: Artificial
<220> FEATURE:
<223> OTHER INFORMATION: Light chain of a particular 280.346.TSY
<220> FEATURE:
<221> NAME/KEY: DOMAIN
<222> LOCATION: (1)..(114)
<223> OTHER INFORMATION: Light chain variable domain (i.e. SEQ ID NO:
      17)
<220> FEATURE:
<221> NAME/KEY: DOMAIN
<222> LOCATION: (115)..(220)
<223> OTHER INFORMATION: Light chain constant domain (i.e. SEQ ID NO:
      19)

<400> SEQUENCE: 21

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Thr Leu Ala Trp Tyr Gln Gln Lys Pro Gly Gln
        35                  40                  45

Pro Pro Lys Leu Leu Ile Tyr Trp Ala Ser Ser Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Phe Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125
```

-continued

| | | | | | | | | | | | | |
|---|---|---|---|---|---|---|---|---|---|---|---|---|
|Glu|Gln|Leu|Lys|Ser|Gly|Thr|Ala|Ser|Val|Val|Cys|Leu|Leu|Asn|Asn|
| |130| | | | |135| | | |140| | | |

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
            165                 170                 175

Ser Thr Tyr Ser Leu Ser Ser Thr Leu Thr Leu Ser Lys Ala Asp Tyr
        180                 185                 190

Glu Lys His Lys Val Tyr Ala Cys Glu Val Thr His Gln Gly Leu Ser
    195                 200                 205

Ser Pro Val Thr Lys Ser Phe Asn Arg Gly Glu Cys
    210                 215                 220

<210> SEQ ID NO 22
<211> LENGTH: 1335
<212> TYPE: DNA
<213> ORGANISM: Artificial
<220> FEATURE:
<223> OTHER INFORMATION: cDNA encoding the heavy chain of a particular
      280.346.TSY

<400> SEQUENCE: 22

```
gaggtgcagc tggtcgagag cggcggaggg ctggtgcagc caggcggaag cttgaggctg      60
tcctgcgccg ccagcggcta cagcatcacc gccgagtaca tgaactgggt gcggcaggcc     120
ccaggcaagg gcctggaatg gatcggcgag atcaaccccg cgccggcac caccacctac     180
aaccagaagt tcaagggcag gttcaccatc agcgtggacc agagcaagaa caccgcctac     240
ctgcagatga acagcctgag ggccgaggac accgccgtgt actactgcgc cagattcgac     300
gcctacttcg actactgggg cagggcacc ctggtgaccg tgagcagcgc tagcaccaag     360
ggccccagcg tgttccccct ggcccccagc agcaagtcca agcggagg aacagccgcc     420
ctgggctgcc tggtgaagga ctacttcccc gagcccgtga ccgtgtcctg aacagcgga     480
gccctgacct ccggcgtgca caccttcccc gccgtgctgc agagcagcgg cctgtacagc     540
ctgagcagcg tggtgacagt gccaagcagc agcctgggaa cccagaccta catctgcaac     600
gtgaaccaca agcccagcaa caccaaggtg gacaagagag tggagcccaa gagctgcgac     660
aagacccata cctgtccacc ctgcccagcc ccccagtgg ccggacccctc cgtgttcctg     720
ttccccccca gcccaagga caccctgatg atcagcagga ccccgaggt gacctgcgtg     780
gtggtggacg tgagccacga ggacccccgag gtgaagttca attggtatgt ggacggcgtg     840
gaggtgcaca acgccaagac caagcccaga gaggaacagt acaacagcac ctacagggtg     900
gtgtccgtgc tgaccgtgct gcaccaggac tggctgaacg gcaaggaata caagtgcaag     960
gtctccaaca aggccctgcc ctccagcatc gagaaaacca tcagcaaggc caagggccag    1020
ccacgggagc cccaggtgta cactactgccc ccatctcggg aagaaatgac caagaaccag    1080
gtgtccctga cctgtctggt gaagggcttt taccccagcg acatcgccgt ggagtgggag    1140
agcaacggcc agcccgagaa caactacaag accacccccc ctgtgctgga cagcgacggc    1200
agcttcttcc tgtacagcaa gctgaccgtg gacaagtcca ggtggcagca gggcaacgtg    1260
ttcagctgca gcgtgatgca cgaggccctg cacaaccact acacacagaa gagcctgagc    1320
ctgtcccccg gcaag                                                     1335
```

<210> SEQ ID NO 23
<211> LENGTH: 660
<212> TYPE: DNA
<213> ORGANISM: Artificial

-continued

<220> FEATURE:
<223> OTHER INFORMATION: cDNA encoding the light chain of a particular
      280.346.TSY

<400> SEQUENCE: 23

```
gacatcgtga tgacccagag ccccgacagc ctggccgtaa gcttgggcga gagggccacc      60
atcaactgca agagcagcca gagcctgctg tattcctcca accagaagaa caccctggcc     120
tggtatcagc agaagcccgg ccagcccccc aagctgctga tctactgggc cagcagccgg     180
gagagcggcg tgcccgacag gttcagcggc agcggctccg gcaccgactt caccctgacc     240
atcagcagcc tgcaggccga ggacgtggcc gtgtactact gccagcagta ctacagctac     300
cccttcacct tcggccaggg caccaaggtg gagatcaaga ggaccgtggc cgcccccagc     360
gtgttcatct ccccccccag cgacgagcag ctgaagagcg gcaccgccag cgtggtgtgc     420
ctgctgaaca acttttaccc ccgggaggcc aaggtgcagt ggaaggtgga caacgccctg     480
cagagcggca acagccagga aagcgtcacc gagcaggaca gcaaggactc cacctacagc     540
ctgagcagca ccctgaccct gagcaaggcc gactacgaga agcacaaggt gtacgcctgc     600
gaggtgaccc accagggcct gtccagcccc gtgaccaaga gcttcaacag gggcgagtgc     660
```

<210> SEQ ID NO 24
<211> LENGTH: 574
<212> TYPE: PRT
<213> ORGANISM: Homo sapiens

<400> SEQUENCE: 24

```
Met Arg Thr Leu Leu Thr Ile Leu Thr Val Gly Ser Leu Ala Ala His
1               5                   10                  15

Ala Pro Glu Asp Pro Ser Asp Leu Leu Gln His Val Lys Phe Gln Ser
            20                  25                  30

Ser Asn Phe Glu Asn Ile Leu Thr Trp Asp Ser Gly Pro Glu Gly Thr
        35                  40                  45

Pro Asp Thr Val Tyr Ser Ile Glu Tyr Lys Thr Tyr Gly Glu Arg Asp
    50                  55                  60

Trp Val Ala Lys Lys Gly Cys Gln Arg Ile Thr Arg Lys Ser Cys Asn
65                  70                  75                  80

Leu Thr Val Glu Thr Gly Asn Leu Thr Glu Leu Tyr Tyr Ala Arg Val
                85                  90                  95

Thr Ala Val Ser Ala Gly Gly Arg Ser Ala Thr Lys Met Thr Asp Arg
            100                 105                 110

Phe Ser Ser Leu Gln His Thr Thr Leu Lys Pro Pro Asp Val Thr Cys
        115                 120                 125

Ile Ser Lys Val Arg Ser Ile Gln Met Ile Val His Pro Thr Pro Thr
    130                 135                 140

Pro Ile Arg Ala Gly Asp Gly His Arg Leu Thr Leu Glu Asp Ile Phe
145                 150                 155                 160

His Asp Leu Phe Tyr His Leu Glu Leu Gln Val Asn Arg Thr Tyr Gln
                165                 170                 175

Met His Leu Gly Gly Lys Gln Arg Glu Tyr Glu Phe Phe Gly Leu Thr
            180                 185                 190

Pro Asp Thr Glu Phe Leu Gly Thr Ile Met Ile Cys Val Pro Thr Trp
        195                 200                 205

Ala Lys Glu Ser Ala Pro Tyr Met Cys Arg Val Lys Thr Leu Pro Asp
    210                 215                 220

Arg Thr Trp Thr Tyr Ser Phe Ser Gly Ala Phe Leu Phe Ser Met Gly
225                 230                 235                 240
```

```
Phe Leu Val Ala Val Leu Cys Tyr Leu Ser Tyr Arg Tyr Val Thr Lys
                245                 250                 255

Pro Pro Ala Pro Pro Asn Ser Leu Asn Val Gln Arg Val Leu Thr Phe
            260                 265                 270

Gln Pro Leu Arg Phe Ile Gln Glu His Val Leu Ile Pro Val Phe Asp
        275                 280                 285

Leu Ser Gly Pro Ser Ser Leu Ala Gln Pro Val Gln Tyr Ser Gln Ile
    290                 295                 300

Arg Val Ser Gly Pro Arg Glu Pro Ala Gly Ala Pro Gln Arg His Ser
305                 310                 315                 320

Leu Ser Glu Ile Thr Tyr Leu Gly Gln Pro Asp Ile Ser Ile Leu Gln
                325                 330                 335

Pro Ser Asn Val Pro Pro Gln Ile Leu Ser Pro Leu Ser Tyr Ala
            340                 345                 350

Pro Asn Ala Ala Pro Glu Val Gly Pro Pro Ser Tyr Ala Pro Gln Val
            355                 360                 365

Thr Pro Glu Ala Gln Phe Pro Phe Tyr Ala Pro Gln Ala Ile Ser Lys
        370                 375                 380

Val Gln Pro Ser Ser Tyr Ala Pro Gln Ala Thr Pro Asp Ser Trp Pro
385                 390                 395                 400

Pro Ser Tyr Gly Val Cys Met Glu Gly Ser Gly Lys Asp Ser Pro Thr
                405                 410                 415

Gly Thr Leu Ser Ser Pro Lys His Leu Arg Pro Lys Gly Gln Leu Gln
            420                 425                 430

Lys Glu Pro Pro Ala Gly Ser Cys Met Leu Gly Gly Leu Ser Leu Gln
        435                 440                 445

Glu Val Thr Ser Leu Ala Met Glu Glu Ser Gln Glu Ala Lys Ser Leu
    450                 455                 460

His Gln Pro Leu Gly Ile Cys Thr Asp Arg Thr Ser Asp Pro Asn Val
465                 470                 475                 480

Leu His Ser Gly Glu Glu Gly Thr Pro Gln Tyr Leu Lys Gly Gln Leu
                485                 490                 495

Pro Leu Leu Ser Ser Val Gln Ile Glu Gly His Pro Met Ser Leu Pro
            500                 505                 510

Leu Gln Pro Pro Ser Arg Pro Cys Ser Pro Ser Asp Gln Gly Pro Ser
        515                 520                 525

Pro Trp Gly Leu Leu Glu Ser Leu Val Cys Pro Lys Asp Glu Ala Lys
    530                 535                 540

Ser Pro Ala Pro Glu Thr Ser Asp Leu Glu Gln Pro Thr Glu Leu Asp
545                 550                 555                 560

Ser Leu Phe Arg Gly Leu Ala Leu Thr Val Gln Trp Glu Ser
                565                 570

<210> SEQ ID NO 25
<211> LENGTH: 116
<212> TYPE: PRT
<213> ORGANISM: Mus musculus
<220> FEATURE:
<221> NAME/KEY: MISC_FEATURE
<223> OTHER INFORMATION: mouse 280.46.3.4 VH (280.46.3.4)

<400> SEQUENCE: 25

Glu Val Gln Leu Gln Gln Ser Gly Pro Glu Leu Val Arg Pro Gly Thr
1               5                   10                  15

Ser Val Lys Ile Ser Cys Lys Ala Ser Gly Tyr Ser Leu Thr Ala Asp
            20                  25                  30
```

```
Tyr Met Asn Trp Val Lys Gln Ser Pro Glu Glu Ser Leu Glu Trp Ile
             35                  40                  45

Gly Glu Ile Asn Pro Ser Thr Gly Thr Thr Tyr Asn Gln Lys Phe
 50                  55                  60

Glu Ala Lys Ala Thr Leu Thr Val Asp Gln Ser Asn Thr Ala Tyr
 65                  70                  75                  80

Leu Gln Leu Thr Ser Leu Thr Ser Glu Asp Ser Ala Val Tyr Tyr Cys
             85                  90                  95

Ala Arg Phe Asp Ala Tyr Phe Asp Tyr Trp Gly Gln Gly Thr Thr Val
                100                 105                 110

Thr Val Ser Ser
             115

<210> SEQ ID NO 26
<211> LENGTH: 114
<212> TYPE: PRT
<213> ORGANISM: Mus musculus

<400> SEQUENCE: 26

Asp Ile Val Met Thr Gln Ser Pro Ser Ser Leu Ala Val Ser Val Gly
 1               5                  10                  15

Glu Lys Val Thr Met Ser Cys Lys Ser Ser Gln Ser Leu Leu Tyr Ser
             20                  25                  30

Ser Asn Gln Lys Asn Cys Leu Ala Trp Tyr Gln Gln Lys Pro Gly Gln
             35                  40                  45

Ser Pro Lys Leu Leu Ile Tyr Trp Ala Ser Ser Arg Glu Ser Gly Val
 50                  55                  60

Pro Asp Arg Phe Thr Gly Ser Gly Ser Gly Thr Asp Phe Thr Leu Thr
 65                  70                  75                  80

Ile Ser Ser Val Lys Thr Glu Asp Leu Ala Val Tyr Tyr Cys Gln Gln
             85                  90                  95

Tyr Phe Ser Tyr Pro Phe Thr Phe Gly Ser Gly Thr Lys Leu Glu Ile
                100                 105                 110

Lys Arg

<210> SEQ ID NO 27
<211> LENGTH: 101
<212> TYPE: PRT
<213> ORGANISM: Homo sapiens
<220> FEATURE:
<221> NAME/KEY: MISC_FEATURE
<223> OTHER INFORMATION: Immunoglobulin kappa variable 4-1 (IGKV4-1)

<400> SEQUENCE: 27

Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Ser Val Leu Tyr Ser
             20                  25                  30

Ser Asn Asn Lys Asn Tyr Leu Ala Trp Tyr Gln Gln Lys Pro Gly Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
             85                  90                  95

Tyr Tyr Ser Thr Pro
```

-continued

```
                100

<210> SEQ ID NO 28
<211> LENGTH: 97
<212> TYPE: PRT
<213> ORGANISM: Artificial
<220> FEATURE:
<223> OTHER INFORMATION: Immunoglobulin heavy variable 3-66 (IGHV3-66)

<400> SEQUENCE: 28

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 29
<211> LENGTH: 113
<212> TYPE: PRT
<213> ORGANISM: Artificial
<220> FEATURE:
<223> OTHER INFORMATION: First version of humanized 280.46.3.4 VL
      (280.VK4-1-C)

<400> SEQUENCE: 29

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Cys Leu Ala Trp Tyr Gln Gln Lys Pro Gly Gln
        35                  40                  45

Pro Pro Lys Leu Leu Ile Tyr Trp Ala Ser Ser Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Tyr Pro Phe Thr Phe Gly Gln Gly Thr Lys Val Glu Ile
            100                 105                 110

Lys

<210> SEQ ID NO 30
<211> LENGTH: 116
<212> TYPE: PRT
<213> ORGANISM: Artificial
<220> FEATURE:
<223> OTHER INFORMATION: First version of humanized 280.46.3.4 VH
      (280.VH3-66.1)

<400> SEQUENCE: 30

Glu Val Gln Leu Val Glu Ser Gly Gly Gly Leu Val Gln Pro Gly Gly
1               5                   10                  15
```

Ser Leu Arg Leu Ser Cys Ala Ala Ser Gly Tyr Ser Leu Thr Ala Asp
            20                  25                  30

Tyr Met Asn Trp Val Arg Gln Ala Pro Gly Lys Gly Leu Glu Trp Ile
            35                  40                  45

Gly Glu Ile Asn Pro Ser Thr Gly Thr Thr Thr Tyr Asn Gln Lys Phe
 50                  55                  60

Glu Ala Arg Ala Thr Leu Thr Val Asp Gln Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Phe Asp Ala Tyr Phe Asp Tyr Trp Gly Gln Gly Thr Leu Val
            100                 105                 110

Thr Val Ser Ser
        115

<210> SEQ ID NO 31
<211> LENGTH: 113
<212> TYPE: PRT
<213> ORGANISM: Artificial
<220> FEATURE:
<223> OTHER INFORMATION: Second version of humanized 280.46.3.4 VL
      (280.VK4-1-S)

<400> SEQUENCE: 31

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Ser Leu Ala Trp Tyr Gln Gln Lys Pro Gly Gln
        35                  40                  45

Pro Pro Lys Leu Leu Ile Tyr Trp Ala Ser Ser Arg Glu Ser Gly Val
 50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Phe Ser Tyr Pro Phe Thr Phe Gly Gln Gly Thr Lys Val Glu Ile
            100                 105                 110

Lys

<210> SEQ ID NO 32
<211> LENGTH: 113
<212> TYPE: PRT
<213> ORGANISM: Artificial
<220> FEATURE:
<223> OTHER INFORMATION: Third version of humanized 280.46.3.4 VL
      (280.VK4-1-T)

<400> SEQUENCE: 32

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
            20                  25                  30

Ser Asn Gln Lys Asn Thr Leu Ala Trp Tyr Gln Gln Lys Pro Gly Gln
        35                  40                  45

Pro Pro Lys Leu Leu Ile Tyr Trp Ala Ser Ser Arg Glu Ser Gly Val
 50                  55                  60

Pro Asp Arg Phe Ser Gly Ser Gly Ser Gly Thr Asp Phe Thr Leu Thr
65                  70                  75                  80

```
Ile Ser Ser Leu Gln Ala Glu Asp Val Ala Val Tyr Tyr Cys Gln Gln
                85                  90                  95

Tyr Phe Ser Tyr Pro Phe Thr Phe Gly Gln Gly Thr Lys Val Glu Ile
               100                 105                 110

Lys

<210> SEQ ID NO 33
<211> LENGTH: 116
<212> TYPE: PRT
<213> ORGANISM: Artificial
<220> FEATURE:
<223> OTHER INFORMATION: Version 4 of the humanized 280.46.3.4 VH
      (280.VH3-66-4)

<400> SEQUENCE: 33

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Leu Thr Ala Asp
            20                  25                  30

Tyr Met Asn Trp Val Arg Gln Ala Pro Gly Lys Gly Leu Glu Trp Ile
             35                  40                  45

Gly Glu Ile Asn Pro Ser Thr Gly Thr Thr Tyr Asn Gln Lys Phe
 50                  55                  60

Lys Gly Arg Ala Thr Leu Ser Val Asp Gln Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Phe Asp Ala Tyr Phe Asp Tyr Trp Gly Gln Gly Thr Leu Val
               100                 105                 110

Thr Val Ser Ser
        115

<210> SEQ ID NO 34
<211> LENGTH: 116
<212> TYPE: PRT
<213> ORGANISM: Artificial
<220> FEATURE:
<223> OTHER INFORMATION: Version 18 of the humanized 280.46.3.4 VH
      (280.VH3-66-18)

<400> SEQUENCE: 34

Glu Val Gln Leu Val Glu Ser Gly Gly Gly Leu Val Gln Pro Gly Gly
 1               5                  10                  15

Ser Leu Arg Leu Ser Cys Ala Ala Ser Gly Tyr Ser Leu Thr Ala Glu
            20                  25                  30

Tyr Met Asn Trp Val Arg Gln Ala Pro Gly Lys Gly Leu Glu Trp Ile
             35                  40                  45

Gly Glu Ile Asn Pro Ser Thr Gly Thr Thr Tyr Asn Gln Lys Phe
 50                  55                  60

Lys Gly Arg Ala Thr Leu Ser Val Asp Gln Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Phe Asp Ala Tyr Phe Asp Tyr Trp Gly Gln Gly Thr Leu Val
               100                 105                 110

Thr Val Ser Ser
        115
```

```
<210> SEQ ID NO 35
<211> LENGTH: 113
<212> TYPE: PRT
<213> ORGANISM: Mus musculus
<220> FEATURE:
<221> NAME/KEY: MISC_FEATURE
<223> OTHER INFORMATION: mouse 280.46.3.4 VL (280.46.3.4)

<400> SEQUENCE: 35

Asp Ile Val Met Thr Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Cys Leu Ala Trp Tyr Gln Gln Lys Pro Gly Gln
        35                  40                  45

Ser Pro Lys Leu Leu Ile Tyr Trp Ala Ser Ser Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Thr Glu Asp Leu Ala Val Tyr Tyr Cys Gln Gln
                85                  90                  95

Tyr Phe Ser Tyr Pro Phe Thr Phe Gly Ser Gly Thr Lys Leu Glu Ile
            100                 105                 110

Lys

<210> SEQ ID NO 36
<211> LENGTH: 111
<212> TYPE: PRT
<213> ORGANISM: Homo sapiens
<220> FEATURE:
<221> NAME/KEY: MISC_FEATURE
<223> OTHER INFORMATION: Immunoglobulin germline heavy variable gene
      3-66 (IGHV3-66)

<400> SEQUENCE: 36

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Phe Asp Tyr Trp Gly Gln Gly Thr Leu Val Thr Val Ser Ser
            100                 105                 110

<210> SEQ ID NO 37
<211> LENGTH: 113
<212> TYPE: PRT
<213> ORGANISM: Artificial Sequence
<220> FEATURE:
<223> OTHER INFORMATION: Final humanized VL (280.VK4-1-TSY)

<400> SEQUENCE: 37

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Tyr Ser
```

```
                20              25                  30
Ser Asn Gln Lys Asn Cys Leu Ala Trp Tyr Gln Gln Lys Pro Gly Gln
            35              40                  45

Pro Pro Lys Leu Leu Ile Tyr Trp Ala Ser Ser Arg Glu Ser Gly Val
        50              55                  60

Pro Asp Arg Phe Ser Gly Ser Gly Ser Gly Thr Asp Phe Thr Leu Thr
65              70              75                  80

Ile Ser Ser Leu Gln Ala Glu Asp Val Ala Val Tyr Tyr Cys Gln Gln
                85              90                  95

Tyr Tyr Ser Tyr Pro Phe Thr Phe Gly Gln Gly Thr Lys Val Glu Ile
            100             105                 110

Lys
```